United States Patent
Perni et al.

(10) Patent No.: US 12,065,405 B2
(45) Date of Patent: *Aug. 20, 2024

(54) PRODRUGS AND CONJUGATES OF DIMETHYLTRYPTAMINE

(71) Applicant: ATAI Therapeutics, Inc., New York, NY (US)

(72) Inventors: Robert B. Perni, Marlborough, MA (US); Glenn Short, Scituate, MA (US); Srinivas G. Rao, Encinitas, CA (US); Tanweer A. Khan, Bridgewater, NJ (US)

(73) Assignee: ATAI Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/299,347

(22) Filed: Apr. 12, 2023

(65) Prior Publication Data

US 2023/0357146 A1 Nov. 9, 2023

Related U.S. Application Data

(63) Continuation of application No. 17/889,013, filed on Aug. 16, 2022, now Pat. No. 11,643,391, which is a continuation of application No. 17/836,984, filed on Jun. 9, 2022, now abandoned.

(60) Provisional application No. 63/229,879, filed on Aug. 5, 2021, provisional application No. 63/208,874, filed on Jun. 9, 2021.

(51) Int. Cl.
| | |
|---|---|
| *C07D 209/16* | (2006.01) |
| *C07D 209/08* | (2006.01) |
| *C07D 209/12* | (2006.01) |
| *C07D 209/14* | (2006.01) |
| *C07D 401/06* | (2006.01) |
| *C07D 403/06* | (2006.01) |
| *C07F 9/572* | (2006.01) |

(52) U.S. Cl.
CPC ......... *C07D 209/16* (2013.01); *C07D 209/08* (2013.01); *C07D 209/12* (2013.01); *C07D 209/14* (2013.01); *C07D 401/06* (2013.01); *C07D 403/06* (2013.01); *C07F 9/5728* (2013.01)

(58) Field of Classification Search
CPC .. C07D 209/16; C07D 209/08; C07D 209/12; C07D 209/14; C07D 401/06; C07D 403/06
See application file for complete search history.

(56) References Cited

U.S. PATENT DOCUMENTS

| | | |
|---|---|---|
| 3,499,003 A | 3/1970 | Welstead, Jr. |
| 5,340,838 A | 8/1994 | Gidda et al. |
| 5,637,593 A | 6/1997 | Porter et al. |
| 5,705,527 A | 1/1998 | Ishihara et al. |
| 6,201,025 B1 | 3/2001 | Dax et al. |
| 6,436,950 B1 | 8/2002 | Achari et al. |
| 8,268,856 B2 | 9/2012 | Hamann et al. |
| 9,388,395 B2 | 7/2016 | Nazor et al. |
| 9,720,005 B2 | 8/2017 | McConnell et al. |
| 11,242,318 B2 | 2/2022 | Nivorozhkin et al. |
| 11,332,441 B2 | 5/2022 | Chadeayne |
| 11,602,521 B2 | 3/2023 | Rao et al. |
| 11,643,391 B2 | 5/2023 | Perni et al. |
| 2002/0115715 A1 | 8/2002 | Dax et al. |
| 2003/0079301 A1 | 5/2003 | Sauter et al. |
| 2004/0235899 A1 | 11/2004 | Maria Assunta et al. |
| 2005/0152858 A1 | 7/2005 | Bertz et al. |
| 2005/0245594 A1 | 11/2005 | Sutter et al. |
| 2005/0250839 A1 | 11/2005 | Marnett et al. |
| 2007/0099909 A1 | 5/2007 | Chen et al. |
| 2008/0248511 A1 | 10/2008 | Daily et al. |
| 2008/0318957 A1 | 12/2008 | Glinka et al. |
| 2010/0113539 A1 | 5/2010 | Scott et al. |
| 2012/0028995 A1 | 2/2012 | Ansorge et al. |
| 2015/0071994 A1 | 3/2015 | Schentag et al. |
| 2015/0346226 A1 | 12/2015 | Mcconnell et al. |

(Continued)

FOREIGN PATENT DOCUMENTS

| | | |
|---|---|---|
| EP | 1336602 A1 | 8/2003 |
| WO | WO-9323364 A1 | 11/1993 |

(Continued)

OTHER PUBLICATIONS

ACS Chem. Neuroscience, 2018, pp. 1582-1590.

(Continued)

*Primary Examiner* — Rebecca L Anderson
(74) *Attorney, Agent, or Firm* — Cooley LLP

(57) ABSTRACT

Provided herein are compounds of Formula (I), or pharmaceutically acceptable salt thereof, wherein $R_1$, $R_2$, $R_3$, $R_4$, $R_5$, $R_8$, $R_9$, X, Y, Z, W, and m are defined herein. Also provided herein are pharmaceutical compositions comprising a compound of Formula (I) or pharmaceutically acceptable salt thereof and a pharmaceutically acceptable excipient.

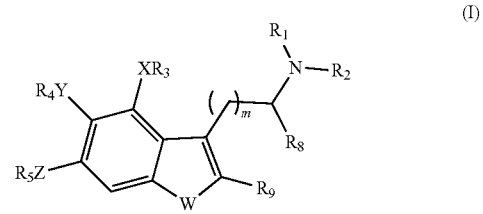

(I)

30 Claims, 5 Drawing Sheets

(56) References Cited

U.S. PATENT DOCUMENTS

| | | |
|---|---|---|
| 2016/0002195 A1 | 1/2016 | Makriyannis et al. |
| 2019/0315689 A1 | 10/2019 | Chen et al. |
| 2020/0325124 A1 | 10/2020 | Lavoie et al. |
| 2020/0390746 A1 | 12/2020 | Rands et al. |
| 2020/0397752 A1 | 12/2020 | Perez Castillo et al. |
| 2021/0085671 A1 | 3/2021 | Chadeayne |
| 2021/0145851 A1 | 5/2021 | Stamets |
| 2021/0236523 A1 | 8/2021 | Schindler et al. |
| 2021/0277433 A1 | 9/2021 | Protzko |
| 2021/0346347 A1 | 11/2021 | Witowski et al. |
| 2021/0353615 A1 | 11/2021 | Chadeayne |
| 2021/0363104 A1 | 11/2021 | Nivorozhkin et al. |
| 2021/0378969 A1 | 12/2021 | Rands et al. |
| 2021/0395201 A1 | 12/2021 | Rands et al. |
| 2022/0031662 A1 | 2/2022 | Terwey |
| 2022/0071958 A1 | 3/2022 | Terwey |
| 2022/0079881 A1 | 3/2022 | Modi |
| 2022/0267267 A1 | 8/2022 | Feilding-Mellen |
| 2022/0304980 A1 | 9/2022 | Arnold et al. |
| 2022/0339139 A1 | 10/2022 | Rao et al. |
| 2022/0388956 A1 | 12/2022 | Short et al. |
| 2023/0041584 A1 | 2/2023 | Perni et al. |
| 2023/0066720 A1 | 3/2023 | Perni et al. |
| 2023/0099972 A1 | 3/2023 | Rao et al. |
| 2023/0227407 A1 | 7/2023 | Perni et al. |
| 2023/0227421 A1 | 7/2023 | Perni et al. |
| 2023/0310374 A1 | 10/2023 | Rao et al. |
| 2023/0322735 A1 | 10/2023 | Kruegel |

FOREIGN PATENT DOCUMENTS

| | | |
|---|---|---|
| WO | WO-9506638 A1 | 3/1995 |
| WO | WO-9617842 A1 | 6/1996 |
| WO | WO-0041755 A1 | 7/2000 |
| WO | WO-0051672 A1 | 9/2000 |
| WO | WO-0211800 A2 | 2/2002 |
| WO | WO-02068029 A2 | 9/2002 |
| WO | WO-02068030 A2 | 9/2002 |
| WO | WO-02068031 A2 | 9/2002 |
| WO | WO-02068032 A2 | 9/2002 |
| WO | WO-03000310 A2 | 1/2003 |
| WO | WO-03020350 A1 | 3/2003 |
| WO | WO-03026559 A2 | 4/2003 |
| WO | WO-03082393 A1 | 10/2003 |
| WO | WO-03084591 A1 | 10/2003 |
| WO | WO-03090812 A2 | 11/2003 |
| WO | WO-2006099416 A1 | 9/2006 |
| WO | WO-2010151258 A1 | 12/2010 |
| WO | WO-2011041870 A1 | 4/2011 |
| WO | WO-2013063492 A1 | 5/2013 |
| WO | WO-2018094106 A2 | 5/2018 |
| WO | WO-2019081764 A1 | 5/2019 |
| WO | WO-2019213551 A1 | 11/2019 |
| WO | WO-2020037372 A1 | 2/2020 |
| WO | WO-2020176597 A1 | 9/2020 |
| WO | WO-2020181194 A1 | 9/2020 |
| WO | WO-2021226416 A1 | 11/2021 |
| WO | WO-2021244831 A1 | 12/2021 |
| WO | WO-2021250434 A1 | 12/2021 |
| WO | WO-2021250435 A1 | 12/2021 |
| WO | WO-2022051670 A1 | 3/2022 |
| WO | WO-2022061242 A1 | 3/2022 |
| WO | WO-2022082058 A1 | 4/2022 |
| WO | WO-2022232179 A1 | 11/2022 |
| WO | WO-2022235514 A1 | 11/2022 |
| WO | WO-2022235529 A1 | 11/2022 |
| WO | WO-2022246572 A1 | 12/2022 |
| WO | WO-2022251351 A1 | 12/2022 |
| WO | WO-2022261383 A1 | 12/2022 |
| WO | WO-2023036473 A1 | 3/2023 |
| WO | WO-2023055992 A1 | 4/2023 |
| WO | WO-2023129956 | 7/2023 |

OTHER PUBLICATIONS

Safety Data Sheet, Caymanchem.com, Cayman Chemical, Apr. 21, 2021, 6 pages., https://cdn.caymanchem.com/cdn/msds/33586m.pdf.

Andersson et al., Psychoactive substances as a last resort—a qualitative study of self-treatment of migraine and cluster headaches, Harm Reduction Journal, Dec. 2017, 10 pages.

Archer et al., 5-Methoxy-N, N-dimethyltryptamine-induced analgesia is blocked by alpha-adrenoceptor antagonists in rats, British J. Pharmac., Oct. 1986, pp. 293-298.

Baker et al., Neurochemical and neuropharmacological investigation of N-cyanoethyltryptamine, a potential prodrug of tryptamine, Proc West Pharmacol Soc., 1987, pp. 307-311.

Barsuglia et al., Intensity of mystical experiences occasioned by 5-MeO-DMT and comparison with a prior psilocybin study, Front. Psychol., Dec. 2018, 6 pages.

Benneyworth et al., Complex discriminative stimulus properties of (+)lysergic acid diethylamide (LSD) in C57Bl/6J mice, Psychopharmacology, 2005, pp. 854-862.

Berge, et al., Pharmaceutical salts, Journal of pharmaceutical sciences, Jan. 1977, pp. 1-9.

Brito-Da-Costa, et al., Toxicokinetics and toxicodynamics of ayahuasca alkaloids N, N-dimethyltryptamine (DMT), harmine, harmaline and tetrahydroharmine: clinical and forensic impact., Pharmaceuticals, Oct. 2020, 36 pages.

Bugaenko, Synthesis of indoles: recent advances, 2019, pp. 99-159.

Cameron et al. A non-hallucinogenic psychedelic analogue with therapeutic potential, Nature, 2021, pp. 474-479.

Carhart-Harris et al., Psilocybin for treatment-resistant depression: fMRI-measured brain mechanisms, Scientific Reports, Oct. 2017, 11 pages.

Carter et al., Modulating the rate and rhythmicity of perceptual rivalry alternations with the mixed 5-HT2A and 5-HT1A agonist psilocybin, Neuropsychopharmacology, Jun. 2005, pp. 1154-1162.

CAS Registry No. 1152718-19-8, Benzenemethanamine, N-[4-(1,1-dimethylethyl)cyclohexyl]-2,4-difluoro-α-methyl-, Jun. 5, 2009, 1 page.

CAS Registry No. 1152826-22-6, Benzenemethanamine, 5-bromo-N-[4-(1,1-dimethylpropyl)cyclohexyl]-2-fluoro-, Jun. 7, 2009, 1 page.

CAS Registry No. 1154138-59-6, Benzenemethanamine, N-[4-(1,1-dimethylpropyl)cyclohexyl]-2,5-difluoro-, Jun. 9, 2009, 1 page.

CAS Registry No. 127456-43-3, Phenol, 2-[[[4-(1,1-dimethylethyl)cyclohexyl]amino]methyl]-4-(1,1-dimethylpropyl)-, trans-(9CI), Jun. 1, 1990, 1 page.

CAS Registry No. 127456-44-4, 1H-Inden-5-ol, 6-[[[4-(1,1-dimethylethyl)cyclohexyl]amino]methyl]-2,3-dihydro-, trans- (9CI), Jun. 1, 1990, 1 page.

CAS Registry No. 127456-45-5, Phenol, 4-(1,1-dimethylethyl)-2-[[[4-(1,1-dimethylethyl)cyclohexyl]amino]methyl]-, trans- (9CI), Jun. 1, 1990, 1 page.

CAS Registry No. 127456-46-6, Phenol, 4-(1,1-dimethylethyl)-2-[[[4-(1,1-dimethylethyl)cyclohexyl]amino]methyl]-6-methyl-, hydrochloride, trans-(9CI), Jun. 1, 1990, 1 page.

CAS Registry No. 127456-52-4, Phenol, 2-[[[4-(1,1-dimethylethyl)cyclohexyl]amino]methyl]-4-(1-methylethyl)-, cis- (9CI), Jun. 1, 1990, 1 page.

CAS Registry No. 127456-56-8, Phenol, 4-chloro-2-[[[4-(1,1-dimethylethyl)cyclohexyl]amino]methyl]-, trans- (9CI), Jun. 1, 1990, 1 page.

CAS Registry No. 127456-57-9, Phenol, 2-[[[4-(1,1-dimethylethyl)cyclohexyl]amino]methyl]-4-fluoro-, trans- (9CI), Jun. 1, 1990, 1 page.

CAS Registry No. 1308467-14-2, 1,2-Benzenediol, 3-[[[4-(1,1-dimethylpropyl)cyclohexyl]amino]methyl]-, Jun. 10, 2011, 1 page.

CAS Registry No. 1405571-87-0, Benzenemethanamine, 2-bromo-N-[4-(1,1-dimethylpropyl)cyclohexyl]-5-fluoro-, Nov. 23, 2012, 1 page.

CAS Registry No. 1406541-63-6, Phenol, 2-chloro-4-[[[4-(1,1-dimethylpropyl)cyclohexyl]amino]methyl]-, Nov. 25, 2012, 1 page.

CAS Registry No. 1411655-23-6, Benzenemethanamine, N-[4-(1,1-dimethylpropyl)cyclohexyl]-2,3-difluoro-, Dec. 5, 2012, 1 page.

(56) References Cited

OTHER PUBLICATIONS

CAS Registry No. 1456349-79-3, Benzenemethanamine, 2,3-dichloro-N-[4-(1,1-dimethylpropyl)cyclohexyl]-, Oct. 6, 2013, 1 page.
CAS Registry No. 1458497-71-6, Benzenemethanamine, 2,4-dichloro-N-[4-(1,1-dimethylethyl)cyclohexyl]-α-methyl-, Oct. 15, 2013, 1 page.
CAS Registry No. 1459328-13-2, Phenol, 2-bromo-4-[[[4-(1,1-dimethylpropyl)cyclohexyl]amino]methyl]-, Oct. 16, 2013, 1 page.
CAS Registry No. 1490220-45-5, Benzenemethanamine, 2-bromo-5-chloro-N-[4-(1,1-dimethylpropyl)cyclohexyl]-, Dec. 8, 2013, 1 page.
CAS Registry No. 1515984-46-9, Benzamide, N-(4-aminocyclohexyl)-3-chloro-N,5-dimethyl-, Jan. 10, 2014, 1 page.
CAS Registry No. 1542027-51-9, Phenol, 3-chloro-2-[[[4-(1,1-dimethylpropyl)cyclohexyl]amino]methyl]-, Feb. 11, 2014, 1 page.
CAS Registry No. 1624268-56-9, Benzamide, 4-[[[4-(1,1-dimethylethyl)cyclohexyl]amino]methyl]-N-methyl-, Sep. 22, 2014, 1 page.
CAS Registry No. 1712122-27-4, Benzenemethanamine, 5-chloro-N-[4-(1,1-dimethylpropyl)cyclohexyl]-2-fluoro-, May 25, 2015, 1 page.
CAS Registry No. 1772618-27-5, Phenol, 3-[[[4-(1,1-dimethylpropyl)cyclohexyl]amino]methyl]-5-fluoro-, Jun. 3, 2015, 1 page.
CAS Registry No. 1775706-37-0, Phenol, 2-chloro-6-[[[4-(1,1-dimethylpropyl)cyclohexyl]amino]methyl]-, Jun. 8, 2015, 1 page.
CAS Registry No. 1858436-76-6, Bicyclo[3.1.0]hexan-2-amine, N-[(3-chloro-5-methylphenyl)methyl]-, Feb. 3, 2016, 1 page.
CAS Registry No. 1931388-10-1, Benzenemethanamine, 2,5-dichloro-N-[4-(1,1-dimethylpropyl)cyclohexyl]-, Jun. 14, 2016, 1 page.
CAS Registry No. 1939264-55-7, Phenol, 4-[[[4-(1,1-dimethylpropyl)cyclohexyl]amino]methyl]-2-fluoro-, Jun. 26, 2016, 1 page.
CAS Registry No. 1939792-99-0, Benzenemethanamine, 5-bromo-2-chloro-N-[4-(1,1-dimethylpropyl)cyclohexyl]-, Jun. 27, 2016, 1 page.
CAS Registry No. 1962333-15-8, Benzenemethanamine, N-[4-(1,1-dimethylpropyl)cyclohexyl]-5-fluoro-2-methyl-, Jul. 29, 2016, 1 page.
CAS Registry No. 2032268-58-7, Cyclohexanecarboxylic acid, 4-[[(3-chloro-5-methylphenyl)methyl]amino]-, Nov. 15, 2016, 1 page.
CAS Registry No. 2199998-08-6, Cyclohexanecarboxylic acid, 2-[[(3-chloro-5-methylphenyl)methyl]amino]-1-methyl-, Mar. 27, 2018, 1 page.
CAS Registry No. 2202151-69-5, Cyclohexanecarboxylic acid, 3-[[(3-chloro-5-methylphenyl)methyl]amino]-, Mar. 30, 2018, 1 page.
CAS Registry No. 2322790-81-6, Benzenemethanamine, N-[4-(1,1-dimethylethyl)cyclohexyl]-3-(trifluoromethyl)-, Jun. 2, 2019, 1 page.
CAS Registry No. 2419600-39-6, Benzenemethanamine, 3-chloro-N-[4-(1,1-dimethylpropyl)cyclohexyl]-5-methyl-, Jun. 5, 2020, 1 page.
CAS Registry No. 415970-94-4, Benzenemethanamine, N-[4-(1,1-dimethylethyl)cyclohexyl]-3,5-dimethoxy-, May 15, 2002, 1 page.
CAS Registry No. 744981-83-7, Phenol, 2,6-dibromo-4-[[[4-(1,1-dimethylethyl)cyclohexyl]amino]methyl]-, Sep. 15, 2004, 1 page.
CAS Registry No. 793633-39-3, Phenol, 4-(1,1-dimethylethyl)-2-[[[trans-4-(1,1-dimethylethyl)cyclohexyl]amino]methyl]-6-methyl-, Dec. 6, 2004, 1 page.
Chegaev, et al., NO-donor melatonin derivatives: synthesis and in vitro pharmacological characterization, Journal of pineal research, May 2007, pp. 371-385.
Chen, et al., Structure-activity relationships in a series of 5-[(2,5-dihydroxybenzyl)amino] salicylate inhibitors of EGF-receptor-associated tyrosine kinase: importance of additional hydrophobic aromatic interactions, Journal of Medicinal Chemistry, Mar. 1994, pp. 845-859.
Clinicaltrials.gov, Effects of Dimethyltryptamine in Healthy Subjects (DMT), Apr. 2020, 9 pages, entire document, especially p. 2 table, p. 4 table row 1. Retrieved on Jun. 24, 2022 from https://clinicaltrials.gov/ct2/show/NCT0435304.
Cocchi et al., Novel Psychoactive Phenethylamines: Impact on Genetic Material, International Journal of Molecular Sciences, 2020, 17 pages.
Corne, A Possible Correlation between Drug-Induced Hallucinations in Man and a Behavioural Response in Mice, Psychopharmacolgia (Berl.), 1967, pp. 65-78.
Custodio et al., 25B-NBOMe, a novel N-2-methoxybenzyl-phenethylamine (NBOMe) derivative, may induce rewarding and reinforcing effects via a dopaminergic mechanism: evidence of abuse potential, Addiction Biology, Nov. 2019, 12 pages.
Dakic et al., Short term changes in the proteome of human cerebral organoids induced by 5-MeO-DMT, Scientific Reports, 2017, 13 pages.
Dalgleish, et al., Transdiagnostic approaches to mental health problems: Current status and future directions, J. Consult Clin Psychology, Mar. 2020, pp. 179-195.
Davis et al., 5-methoxy-N, N-dimethyltryptamine (5-MeO-DMT) used in a naturalistic group setting is associated with unintended improvements in depression and anxiety, The American Journal of Drug and Alcohol Abuse, 2019, 10 pages.
De Barros et al., Synthesis of 25X-BOMes and 25X-NBOHs (X=H, I, Br) for pharmacological studies and as reference standards for forensic purposes, Tetrahedron Letters, Mar. 2021, 4 pages.
Dunlap et al., Identification of psychoplastogenic N, N-dimethylaminoisotryptamine (isoDMT) analogues through structure-activity relationship studies, J. Med. Chem. 2020, pp. 1142-1155.
Durham, Regulation of calcitonin gene-related peptide secretion by a serotonergic antimigraine drug, The Journal of Neuroscience, May 1999, pp. 3423-3429.
Glennon et al., Influence of amine substituents on 5-HT2A versus 5-HT2C binding of phenylalkyl-and indolylalkylamines, Journal of Medicinal Chemistry, 1994, pp. 1929-1935.
Gonzalez-Maeso et al., Hallucinogens Recruit Specific Cortical 5-HT2A Receptor-Mediated Signaling Pathways to Affect Behavior, Neuron, Feb. 2007, pp. 439-452.
Gribble, Recent developments in indole ring synthesis-methodology and applications, Journal of the Chemical Society, Perkin Transactions, 2000, pp. 1045-1075.
Halberstadt et al., Differential contributions of serotonin receptors to the behavioral effects of indoleamine hallucinogens in mice, J Psychopharmacol., Nov. 2011, pp. 1548-1561.
Halberstadt, Recent Advances in the Neuropsychopharmacology of Serotonergic Hallucinogens, Behav. Brain Res., 2015, pp. 99-120.
Hamada et al., Water-soluble prodrugs of dipeptide HIV protease inhibitors based on O→N intramolecular acyl migration: Design, synthesis and kinetic study, Bioorg Med Chem., Jan. 2004, pp. 159-170.
Hansen et al., Synthesis and pharmacological evaluation of N-benzyl substituted 4-bromo-2,5-dimethoxyphenethylamines as 5-HT2A/2C partial agonists, Bioorganic & Medicinal Chemistry, 2015, pp. 3933-3937.
Hansen et al., Synthesis and Structure-Activity Relationships of N-Benzyl Phenethylamines as 5-HT2A/2C Agonists, ACS Chemical Neuroscience, 2014, pp. 243-249.
Harriott et al., Animal models of migraine and experimental techniques used to examine trigeminal sensory processing, The Journal of Headache and Pain, 2019, 15 pages.
Healthline, How Long Does DMT Last?, Nov. 2019, 12 pages, entire document, especially p. 1 para 1-3. Retrieved om Jun. 24, 2022 from https://www.healthline.com/health/how-long-does-dmt-last.
Humphrey, et al., Practical methodologies for the synthesis of indoles, Chem. Review, Jul. 2006, pp. 2875-2911.
Huttunen (Prodrugs-from Serendipity to Rational Design, Pharmacal Rev 2011, pp. 750-771.
International Search Report and Written Opinion for International Application No. PCT/US2022/026396, mailed Jul. 28, 2022, 10 pages.
International Search Report and Written Opinion for International Application No. PCT/US2022/030912, mailed Oct. 5, 2022, 20 pages.

(56) References Cited

OTHER PUBLICATIONS

International Search Report and Written Opinion for International Application No. PCT/US2022/032918, mailed Oct. 12, 2022, 10 pages.

International Search Report and Written Opinion for International Application No. PCT/US2022/045336 dated Jan. 13, 2023, 14 pages.

Invitation to Pay Fee for International Application No. PCT/US2022/082465 dated Mar. 16, 2023, 3 pages.

Kaminska et al., 25C-NBOMe short characterization, Forensic Toxicology, 2020, pp. 490-495.

Klein, et al., Structure-Activity Relationships in Potentially Hallucinogenic N,N-Dialkyltryptamines Substituted in the Benzene Moiety, J. Med. Chen, 1982, pp. 908-913.

Klein et al., Toward selective drug development for the human 5-hydroxytryptamine 1E receptor: a comparison of 5-hydroxytryptamine 1E and 1F receptor structure-affinity relationships, The Journal of Pharmacology and Experimental Therapeutics, 2011, pp. 860-867.

Kraehenmann et al., Dreamlike effects of LSD on waking imagery in humans depend on serotonin 2A receptor activation, Psychopharmacology, 2017, pp. 2031-2046.

Kraehenmann et al., LSD Increases Primary Process Thinking via Serotonin 2A Receptor Activation, Front. Pharmacol., 2017, 9 pages.

Kucklander, et al., Darstellung und Oxidation von 2-(2, 5-Dihydroxyphenyl)-ethylamin-Derivaten, II/Synthesis and Oxidation of 2-(2, 5-Dihydroxyphenyl)-ethylamine Derivatives, II. Zeitschrift für Naturforschung B, 1987, pp. 1567-1577 (with English abstract).

Li et al., Treatment of breast and lung cancer cells with a N-7 benzyl guanosine monophosphate tryptamine phosphoramidate pronucleotide (4Ei-1) results in chemosensitization to gemcitabine and induced eIF4E proteasomal degradation, Mol Pharm., Feb. 2013, pp. 523-531.

Lima da Cruz et al., Corrigendum: A Single Dose of 5-MeO-DMT Stimulates Cell Proliferation, Neuronal Survivability, Morphological and Functional Changes in Adult Mice Ventral Dentate Gyrus, Front. Mol. Neurosci., 2018, 11 pages.

Lyon et al., Indolealkylamine analogs share 5-HT2 binding characteristics with phenylalkylamine hallucinogens, European Journal of Pharmacology, 1988, pp. 291-297.

Madsen et al., Psilocybin-induced reduction in chronic cluster headache attack frequency correlates with changes in hypothalamic functional connectivity, Neuropsychopharmacology, 2019, pp. 1328-1334.

Madsen et al., Psychedelic effects of psilocybin correlate with serotonin 2A receptor occupancy and plasma psilocin levels, Neuropsychopharmacology (2019) 44: 1328-1334.

McBride, Bufotenine: Toward an Understanding of Possible Psychoactive Mechanisms, Journal of Psychoactive Drugs, Jul.-Sep. 2000, pp. 321-331.

Melting Point Determination, Melting Range, 2012, 4 pages.

Milne et al., Metabolic engineering of *Saccharomyces cerevisiae* for the de novo production of psilocybin and related tryptamine derivatives, Metabolic Engineering, Jul. 2020, pp. 25-36.

Mithoefer et al., The safety and efficacy of±3,4-methylenedioxymethamphetamine-assisted psychotherapy in subjects with chronic, treatment-resistant posttraumatic stress disorder: the first randomized controlled pilot study, Journal of Psychopharmacology, Apr. 2010, pp. 439-452.

Nichols, Hallucinogens, Pharmacol. Ther., 2004, pp. 131-181.

Nichols, Structure-Activity Relationships of Phenethylamine Hallucinogens, J. Pharm. Sciences, 1981, pp. 839-849.

Ott, J., Pharmepena-psychonautics: human intranasal, sublingual and oral pharmacology of 5-methoxy-N, N-dimethyl-tryptamine, Journal of Psychoactive Drugs, Dec. 2001, pp. 403-407.

Ott, J., Pharmañopo-Psychonautics: Human intranasal, sublingual, intrarectal, pulmonary and oral pharmacology of bufotenine, Journal of Psychoactive Drugs, Sep. 2001, pp. 273-281.

Pokorny et al., Modulatory effect of the 5-HT1A agonist buspirone and the mixed non-hallucinogenic 5-HT1A/2A agonist ergotamine on psilocybin-induced psychedelic experience, Eur. Neuropsychopharmacol., Apr. 2016, pp. 756-766.

Pottie, et al., Identification of psychedelic new psychoactive substances (NPS) showing biased agonism at the 5-HT2AR through simultaneous use of β-arrestin 2 and miniGαq bioassays, Biochemical pharmacology, Dec. 2020, 38 pages.

Preller et al., Effects of serotonin 2A/1A receptor stimulation on social exclusion processing, PNAS, May 3, 2016, vol. 113, No. 18, 5119-5124.

Preller et al., Role of the 5-HT2A Receptor in Self- and Other-Initiated Social Interaction in Lysergic Acid Diethylamide-Induced States: A Pharmacological fMRI Study, J. Neurosci., Apr. 2018, 38(14): 3603-3611.

Preller et al., The Fabric of Meaning and Subjective Effects in LSD-Induced States Depend on Serotonin 2A Receptor Activation, Current Biology, Feb. 2017, pp. 451-457.

PubChem SID 385740476, 2-(2,5-dimethoxy-4-(propan-2-yt)phenyl)-N-(2methoxybenzyl)ethanamine, Sep. 23, 2019, 6 pages, retrieved from https://pubchem.ncbi.nlm.nih.gov/substance/385740476.

Pubchem, SID 627609, Sep. 2004, 8 pages. Retrieved from the Internet: https://pubchem.ncbi.nlm.nih.gov/substance/627609.

PubChem-SID-310331158, Modify Date: Feb. 15, 2015, p. 2.

PubChem-SID-369863280, Modify Date: May 25, 2018, p. 2.

Puledda et al., An update on migraine: current understanding and future directions, J Neurol (2017) 264:2031-2039.

Ray, T., Psychedelics and the Human Receptorome, PLoS ONE (2010) 5(2): e9019, 17 pages.

Roth et al., High-affinity Agonist Binding Is Not Sufficient for Agonist Efficacy at 5-Hydroxytryptamine2A Receptors: Evidence in ,Favor of a Modified Ternary Complex Model, The Journal of Pharmacology and Experimental Therapeautics, 1997, vol. 280, No. 2, pp. 576-583.

Ruiz et al, Routes of Drug Administration: Dosage, Design, and Pharmacotherapy Success, Routes of Drug Administration, Chapter 6, Jan. 2018, 1-43 (Year: 2018).

Sargent et al., Radiohalogen-Labeled Imaging Agents. 3. Compounds for Measurement of Brain Blood Flow by Emission Tomography, Journal of Medicinal Chemistry (1984), 27(8), 1071-1077.

Schifano et al., New psychoactive substances (NPS) and serotonin syndrome onset: A systematic review, Experimental Neurology (2021), 339, 113638 (Author manuscript, 29 pages).

Shen et al., Psychedelic 5-Methoxy-N,N-dimethyltryptamine: Metabolism, Pharmacokinetics, Drug Interactions, and Pharmacological Actions, Curr Drug Metab., Oct. 2010 ; 11(8): 659-666, 18 pages.

Sherwood, A.M., et al., Synthesis and Characterization of 5-MeO-DMT Succinate for Clinical Use, Dec. 2, 2020, ACS Omega 2020, 5, 49, 32067-32075, https://doi.org/10.1021/acsomega.0c05099; entire document, especially abstract.

Sigma Succinic acid—Butanedioic acid, 2023, 4 pages.

Strassman, N-dimethyltryptamine in humans: II. Subjective effects and preliminary results of a new rating scale, Archives of general psychiatry, Feb. 1994, pp. 98-108.

Substance Record for SID 433987242 to PubChem (hereinafter, PubChem '242), Sep. 2020, 7 pages.

The product Item No. 33586 of Cayman Chemical, Apr. 2021, 1 page.

Tirapegui et al., Synthesis of N-(halogenated) benzyl analogs of superpotent serotonin ligands, J. Chil. Chem. Soc., (2014) 59, No. 3, pp. 2625-2627.

Titeler et al., Radioligand binding evidence implicates the brain 5-HT2 receptor as a site of action for LSD and phenylisopropylamine hallucinogens, Psychopharmacology (1988) 94, 213-216.

Tomaszewski et al., Benzofuran Bioisosteres of Hallucinogenic Tryptamines, J. Med. Chem., 1992, 35, pp. 2061-2064.

United States Patent and Trademark Office, International Search Report and Written Opinion for International Application No. PCT/US2022/032715 dated Nov. 17, 2022, 18 pages.

United States Patent and Trademark Office, International Search Report and Written Opinion for PCT/US2022/45336, Jan. 13, 2023, 14 pages.

United States Patent and Trademark Office, International Search Report and Written Opinion for International Application No. PCT/US2022/082465 dated Jun. 6, 2023, 11 pages.

(56) References Cited

OTHER PUBLICATIONS

Uthaug et al., A single inhalation of vapor from dried toad secretion containing 5-methoxy-N,N-dimethyltryptamine (5-MeO-DMT) in a naturalistic setting is related to sustained enhancement of satisfaction with life, mindfulness-related capacities, and a decrement of psychopathological symptoms, Psychopharmacology (2019) 236:2653-2666.
Uthaug et al., Prospective examination of synthetic 5-methoxy-N,N-dimethyltryptamine inhalation: effects on salivary IL-6, cortisol levels, affect, and non-judgment, Psychopharmacology (2020) 237:773-785.
Valle et al., Inhibition of alpha oscillations through serotonin-2A receptor activation underlies the visual effects of ayahuasca in humans, Eur. Neuropsychopharm (2016) 26, 1161-1175 (Author-edited version, 23 pages).
Vollenweider et al., Psilocybin induces schizophrenia-like psychosis in humans via a serotonin-2 agonist action, Neuroreport (1998) 9, 3897-3902 (8 pages).
Vollenweider et al., Psychedelic drugs: neurobiology and potential for treatment of psychiatric disorders, Nature Reviews Neuroscience, Nov. 2020, vol. 21, pp. 611-624.
Wang et al., Anti-inflammatory and analgesic actions of bufotenine through inhibiting lipid metabolism pathway, Biomedicine & Pharmacotherapy (2021) 140: 111749, 11 pages.
Wey, Structure-based design, synthesis, and biological evaluation of indomethacin derivatives as cyclooxygenase-2 inhibiting nitric oxide donors, Journal of medicinal chemistry, Dec. 2007, pp. 6367-82.
Wikipedia, Perfusion, Dec. 29, 2020 (Dec. 29, 2020), retrieved on Jun. 24, 2022 from https://en.wikipedia.org/w/index.php?title=Perfusion&oldid=996968059; entire document, especially p. 1 para 1.
Winter et al., Psilocybin-induced stimulus control in the rat Pharmacol. Biochem. Behav. (2007) 87, 472-480 (18 pages).
Winter et al., The Paradox of 5-Methoxy-N,N-Dimethyltryptamine: An Indoleamine Hallucinogen That Induces Stimulus Control via 5-HT1A Receptors, Pharmacology Biochemistry and Behavior, 2000, vol. 65, No. 1, pp. 75-82.
Wood et al., Prevalence of use and acute toxicity associated with the use of NBOMe drugs, Clinical Toxicology, 2015, 53:85-92.
Yu, Indolealkylamines: Biotransformations and Potential Drug-Drug Interactions, The AAPS Journal, Jun. 2008, vol. 10, No. 2, pp. 242-253.
Abiero et al., "Four Novel Synthetic Tryptamine Analogs Induce Head-Twitch Responses and Increase 5-HTR2a in the Prefrontal Cortex in Mice", Biomol Ther (Seoul). Jan. 1, 2020; 28(1): 83-91.
Barker, "Administration of N,N-dimethyltryptamine (DMT) in psychedelic therapeutics and research and the study of endogenous DMT", Psychopharmacology (Berl). Jun. 2022; 239(6): 1749-1763. Epub Jan. 22, 2022, with erratum, 16 pages.
Buchwald, Peter, "Soft drugs: design principles, success stories, and future perspectives", Expert Opin Drug Metab Toxicol. Aug. 2020; 16(8): 645-650. Epub Jun. 20, 2020.
Carhart-Harris et al., The Therapeutic Potential of Psychedelic Drugs: Past, Present and Future, Neuropsychopharmacology; 42, 2105-2113 (2017). 9 pages.
Davis, et al., "The epidemiology of 5-methoxy-N, N-dimethyltryptamine (5-MeO-DMT) use: Benefits, consequences, patterns of use, subjective effects, and reasons for consumption", J Psychopharmacol, Jul. 2018; 32(7): 779-792. Epub Apr. 30, 2018.
Glennon et al., "Synthesis and evaluation of a novel series of N,N-dimethylisotryptamines", J Med Chem. Jan. 1984; 27(1): 41-5.
Grundke et al., "Photochemical α-Aminonitrile Synthesis Using Zn-Phthalocyanines as Near-Infrared Photocatalysts", J Org Chem. May 6, 2022; 87(9): 5630-5642, with supporting info. Epub Apr. 14, 2022. 60 pages.
Gurevich and Gurevich, "GPCR Signaling Regulation: The Role of GRKs and Arrestins", Front Pharmacol. Feb. 19, 2019: 10: 125. eCollection 2019, 11 pages.
International Preliminary Report on Patentability for International Application No. PCT/US2022/026396 dated Nov. 9, 2023, 8 pages.
International Preliminary Report on Patentability for International Application No. PCT/US2022/032918 dated Dec. 21, 2023, 7 pages.
International Search Report and Written Opinion for International Application No. PCT/US2023/073574 dated Feb. 16, 2024, 12 pages.
Invitation to Pay Additional Fees for International Application No. PCT/US2022/030912, mailed Jul. 28, 2022, 8 pages.
Invitation to Pay Additional Fees for International Application No. PCT/US2022/032918, mailed Aug. 12, 2022, 2 pages.
Invitation to pay additional fees for International Application No. PCT/US2023/073574, dated Nov. 6, 2023, 2 pages.
Krise, J. P., et al., "Novel prodrug approach for tertiary amines: synthesis and preliminary evaluation of N-phosphonooxymethyl prodrugs", J Med Chem. Aug. 12, 1999; 42(16): 3094-100.
McClure-Begley and Roth, "The promises and perils of psychedelic pharmacology for psychiatry", Nat Rev Drug Discov. Jun. 2022; 21(6): 463-473. Epub Mar. 17, 2022.
Mertens and Preller, "Classical Psychedelics as Therapeutics in Psychiatry—Current Clinical Evidence and Potential Therapeutic Mechanisms in Substance Use and Mood Disorders", Pharmacopsychiatry. Jul. 2021; 54(4): 176-190. Epub Jan. 20, 2021.
National Center for Biotechnology Information (2023). PubChem Substance Record for SID 309311543, SID 309311543, Source: Aurora Fine Chemicals LLC. Modified Jan. 30, 2016, retrieved Nov. 7, 2023 from https://pubchem.ncbi.nlm.nih.gov/substance/309311543, 5 pages.
Olson, David E., "The Subjective Effects of Psychedelics May Not Be Necessary for Their Enduring Therapeutic Effects", ACS Pharmacol Transl Sci. Apr. 9, 2021; 4(2): 563-567. Published online Dec. 10, 2020.
Pandy-Szekeres et al., "GPCRdb in 2023: state-specific structure models using AlphaFold2 and new ligand resources", Nucleic Acids Res. Jan. 6, 2023; 51(D1): D395-D402. 8 pages.
Riba, et al., "Metabolism and urinary disposition of N,N-dimethyltryptamine after oral and smoked administration: a comparative study", Drug Test Anal. May 2015;7(5): 401-6. Epub Jul. 28, 2014.
Schindler et al., "Exploratory Controlled Study of the Migraine-Suppressing Effects of Psilocybin", Neurotherapeutics, Jan. 2021; 18(1): 534-543. Epub Nov. 12, 2020. 10 pages.
Sizemore, T.R, and Dacks, A.M., "Circadian Clocks: Mosquitoes Master the Dark Side of the Room", Curr Biol. Aug. 17, 2020; 30(16): R932-R934.
Strassman, "Dose-response study of N,N-dimethyltryptamine in humans. I. Neuroendocrine, autonomic, and cardiovascular effects", Arch Gen Psychiatry. Feb. 1994; 51(2): 85-97.
Terry, Alvin V., "Drugs that target serotonergic receptors", Cognitive Enhancing Drugs, Introduction, pp. 79-80, 2004, 2 pages.
Third Party Observation received for International Application No. PCT/US2022/045336, filed May 24, 2023 and received Jun. 2, 2023, 8 pages.
Zamberlan et al., "The Varieties of the Psychedelic Experience: A Preliminary Study of the Association Between the Reported Subjective Effects and the Binding Affinity Profiles of Substituted Phenethylamines and Tryptamines", Front Integr Neurosci. Nov. 8, 2018: 12: 54. eCollection 2018. 22 pages.

D

PH-VLS-02-23-0

PH-VLS-02-23-10

PRODRUGS AND CONJUGATES OF DIMETHYLTRYPTAMINE

CROSS-REFERENCE TO RELATED APPLICATIONS

The present application is a continuation of U.S. application Ser. No. 17/889,013 filed Aug. 16, 2022, which is a continuation of U.S. application Ser. No. 17/836,984 filed Jun. 9, 2022, which claims priority to U.S. Provisional Patent Application No. 63/208,874 filed Jun. 9, 2021, and U.S. Provisional Application No. 63/229,879 filed Aug. 5, 2021, the contents of which are hereby incorporated by reference in their entirety.

BACKGROUND OF THE INVENTION

N,N-dimethyltryptamine (DMT) is a naturally occurring compound found in numerous plant species and botanical preparations, such as the hallucinogenic infusion known as ayahuasca, and classified as a classic serotonergic psychedelic that induces intense modifications in perception, emotion, and cognition in humans. At higher doses, DMT has a rapid onset, intense psychedelic effects, and a relatively short duration of action with an estimated half-life of less than fifteen minutes. Like other hallucinogens in the tryptamine family, DMT binds to serotonin receptors to produce euphoria and psychedelic effects. Unfortunately, DMT is metabolically unstable and is readily converted by monoamine oxidases (MAO's) to indoleacetic acid and N-oxidation metabolites resulting in poor oral bioavailability.

Serotonergic psychedelics have also demonstrated promising antidepressant, anxiolytic, and anti-addictive properties.

There remains a need for improved prodrugs of tryptamines, such as N,N-dimethyltryptamine (DMT).

SUMMARY OF THE INVENTION

In one aspect, the present disclosure provides a compound of Formula (I):

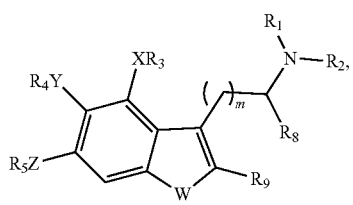

(I)

or a pharmaceutically acceptable salt thereof;
wherein, $R_1$ and $R_2$ are independently hydrogen, alkyl, cycloalkyl, —or $R_1$ and $R_2$ together with the atoms to which they are attached form a heterocycle; X, Y and Z are independently hydrogen, halogen, —O—, —S—, —$NR_A$—, or —(P=O)—$OR_A$(—OR'), wherein $R_A$ is hydrogen or alkyl;

R', $R_3$, $R_4$, $R_5$ and $R_6$ are independently absent, hydrogen, alkyl, —(C=O)-alkyl, —(C=O)$CHR_7$($NH_2$), —(C=O)$(CH_2)_n$($NH_2$), —(C=O)CH($NH_2$)$(CH_2)_n$ ($NH_2$), —(C=O)$(CH_2)_n$(NH)(C=NH)— $NH_2$, —(C=O)$(CH_2)_n$(NH)(C=NH)—$NH_2$ or

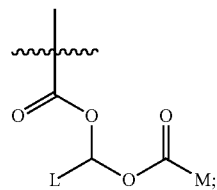

$R_7$ and $R_8$ are independently hydrogen or alkyl;
$R_9$ is hydrogen, alkyl, or halogen, preferably a bromo
L and M are independently alkyl or aryl;
W is oxygen, sulfur or $NR_6$;
n is an integer from 2-7; and
m is an integer from 1-4,
wherein at least one of R', $R_3$, $R_4$, $R_5$ and $R_6$ is —(C=O)-alkyl, —(C=O)$CHR_7$($NH_2$), —(C=O)$(CH_2)_n$($NH_2$), —(C=O)CH($NH_2$)$(CH_2)_n$($NH_2$), —(C=O)$(CH_2)_n$ (NH)(C=NH), —$NH_2$ or

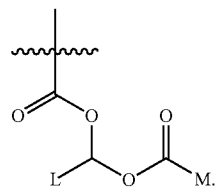

In some embodiments, the compound of Formula (I) is a compound of the Formula (IV):

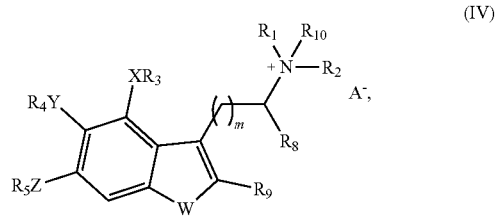

(IV)

wherein $R_{10}$ is —(C=O)-alkyl, —(C=O)$CHR_7$($NH_2$), —(C=O)$(CH_2)_n$($NH_2$), —(C=O)CH($NH_2$)$(CH_2)_n$ ($NH_2$), —(C=O)$(CH_2)_n$(NH)(C=NH)—$NH_2$ or

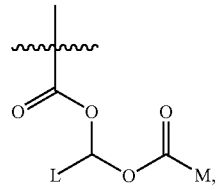

A is a pharmaceutically acceptable anion and
wherein $R_1$, $R_2$, $R_3$, $R_4$, $R_5$, $R_8$, $R_9$, X, Y, Z, W, and m are defined herein.

In some embodiments, the compound of Formula (I) is a compound of the formula:

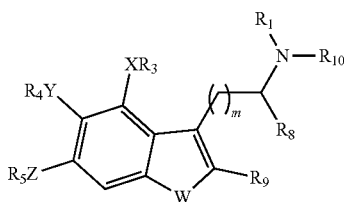

wherein $R_1$, $R_{10}$, $R_3$, $R_4$, $R_5$, $R_8$, $R_9$, X, Y, Z, W, and m are defined herein.

In some embodiments, the present disclosure provides a compound of Formula (III):

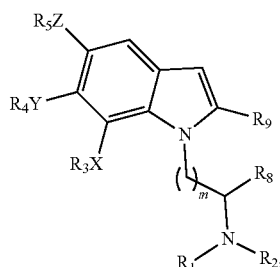

(III)

or a pharmaceutically acceptable salt thereof;
wherein,
$R_1$ and $R_2$ are independently hydrogen, alkyl, cycloalkyl, —or $R_1$ and $R_2$ together with the atoms to which they are attached form a heterocycle;

X, Y and Z are independently hydrogen, halogen, —O—, —S—, —$NR_A$—, or —(P=O)—$OR_A$(—OR'), wherein $R_A$ is hydrogen or alkyl, R', $R_3$, $R_4$, and $R_5$ are independently absent, hydrogen, alkyl, —(C=O)-alkyl, —(C=O)$CHR_7(NH_2)$, —(C=O)$(CH_2)_n(NH_2)$, —(C=O)$CH(NH_2)(CH_2)_n(NH_2)$, —(C=O)$CH(NH_2)(CH_2)_n(NH)(C=NH)$—$NH_2$, —(C=O)$(CH_2)_n(NH)(C=NH)$—$NH_2$ or

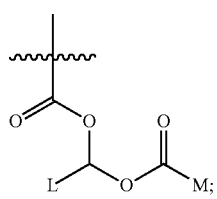

$R_7$ and $R_8$ are independently hydrogen or alkyl;
$R_9$ is hydrogen, alkyl, or halogen;
L and M are independently alkyl or aryl;
n is an integer from 2-7; and
m is an integer from 1-4,
wherein at least one of R', $R_3$, $R_4$, and $R_5$ is —(C=O)-alkyl, —(C=O)$CHR_7(NH_2)$, —(C=O)$(CH_2)_n(NH_2)$, —(C=O)$CH(NH_2)(CH_2)_n(NH_2)$, —(C=O)$(CH_2)_n(NH)(C=NH)$—$NH_2$ or

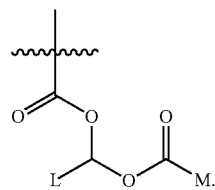

In some embodiments, the compound of Formula (V) is a compound of the formula:

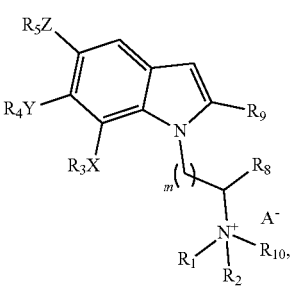

(V)

wherein $R_{10}$ is —(C=O)-alkyl, —(C=O)$CHR_7(NH_2)$, —(C=O)$(CH_2)_n(NH_2)$, —(C=O)$CH(NH_2)(CH_2)_n(NH_2)$, —(C=O)$CH(NH_2)(CH_2)_n(NH)(C=NH)$—$NH_2$, —(C=O)$(CH_2)_n(NH)(C=NH)$—$NH_2$ or

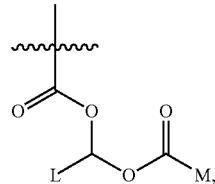

A is a pharmaceutically acceptable anion,
and wherein $R_1$, $R_2$, $R_3$, $R_4$, $R_5$, $R_8$, $R_9$, X, Y, Z, and m are defined herein.

In some embodiments, the present disclosure provides a pharmaceutical composition comprising a compound of Formula (I) or a pharmaceutically acceptable salt thereof and a pharmaceutically acceptable excipient.

In some embodiments, the present disclosure provides a pharmaceutical composition comprising a compound of Formula (II) or a pharmaceutically acceptable salt thereof and a pharmaceutically acceptable excipient.

DETAILED DESCRIPTION

Figure 1A:
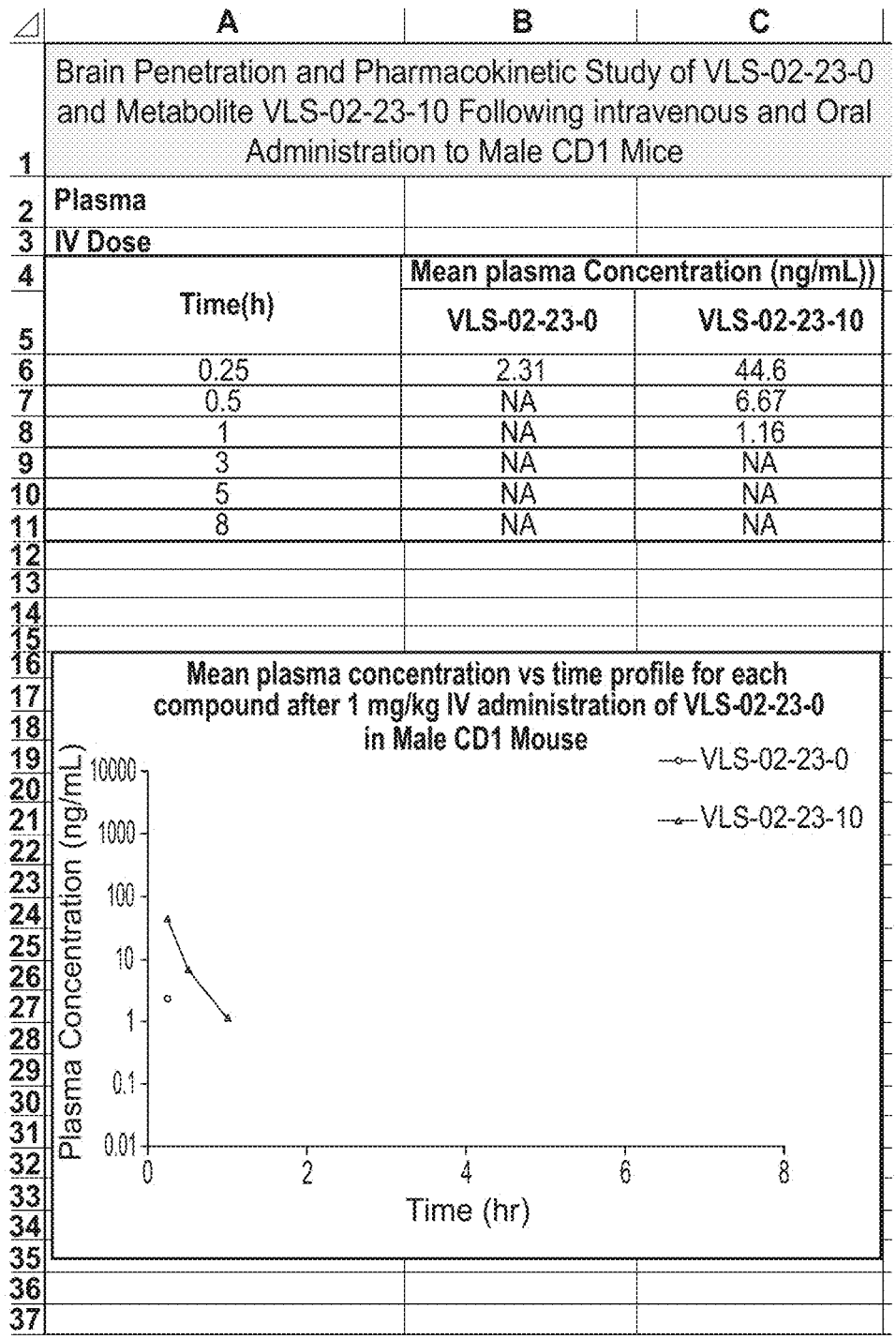
FIGS. 1A-1C show PK studies of N-phosphonooxymethyl prodrug 6-1-2 (VLS-02-23-0) and metabolite (VLS-02-023-10) following intravenous (1 mg/kg) and oral administration (30 mg/kg) to male CD1 mice (in plasma).
Figure 1B:
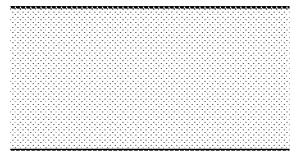
Figure 1B:
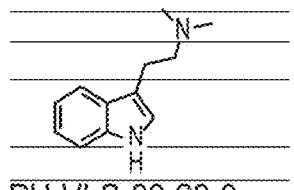
Figure 1C:
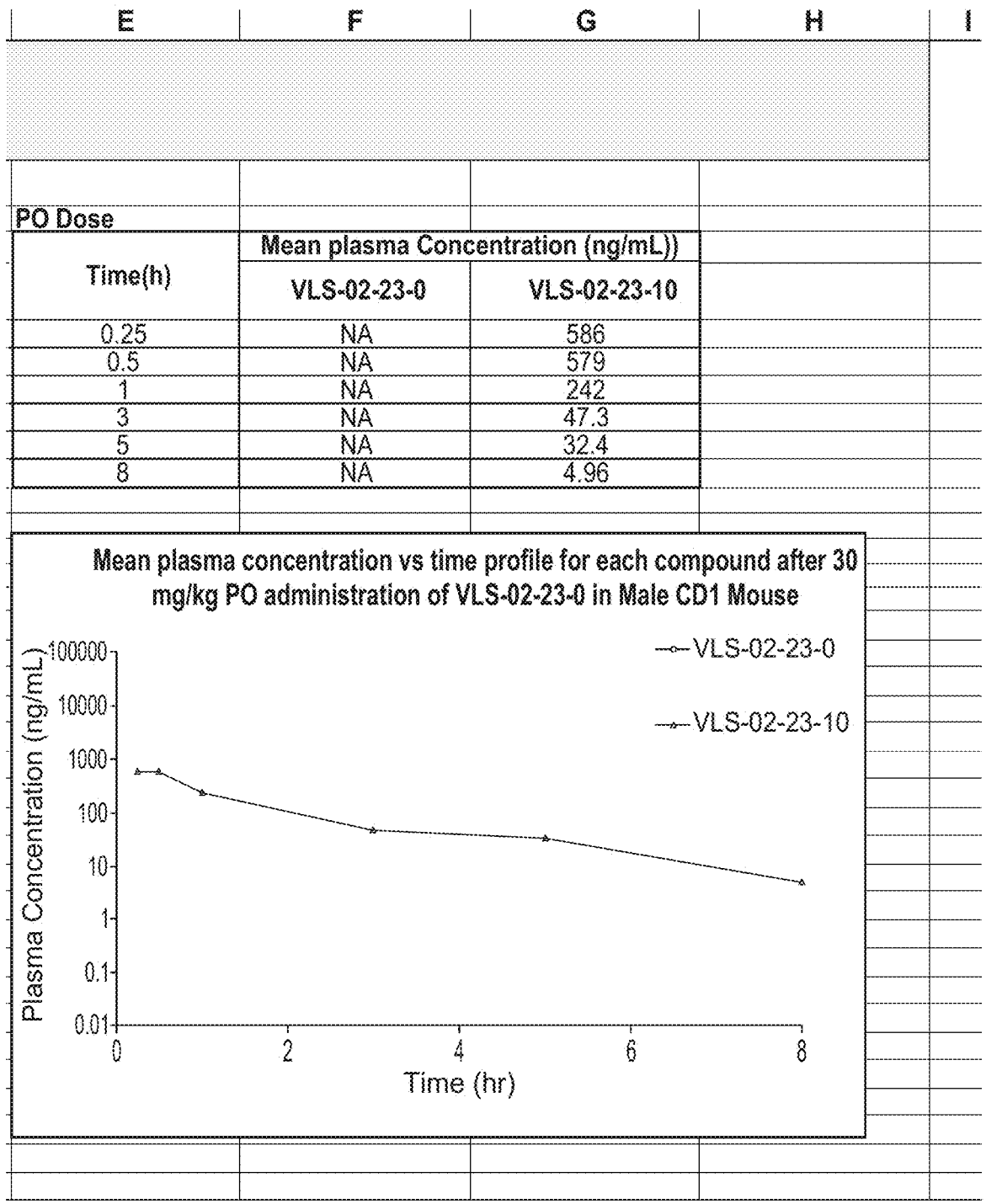

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms "administer," "administering" or "administration" as used herein refer to administering a compound or pharmaceutically acceptable salt of the compound or a composition or formulation comprising the compound or pharmaceutically acceptable salt of the compound to a patient.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

The term "treating" as used herein with regard to a patient, refers to improving at least one symptom of the patient's disorder. In some embodiments, treating can be improving, or at least partially ameliorating a disorder or one or more symptoms of a disorder.

The term "preventing" as used herein with regard to a patient or subject, refers to preventing the onset of disease development if none had occurred, preventing the disease or disorder from occurring in a subject or a patient that may be predisposed to the disorder or disease but has not yet been diagnosed as having the disorder or disease, and/or preventing further disease/disorder development if already present.

The term "therapeutically effective" applied to dose or amount refers to that quantity of a compound or pharmaceutical formulation that is sufficient to result in a desired clinical benefit after administration to a patient in need thereof.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Aryl" refers to a hydrocarbon ring system comprising hydrogen, 6 to 18 carbon atoms and at least one aromatic ring, and which is attached to the rest of the molecule by a single bond. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the "aryl" can be optionally substituted.

"Cycloalkyl" refers to a stable non-aromatic monocyclic or polycyclic fully saturated hydrocarbon consisting solely of carbon and hydrogen atoms, which can include fused, bridged, or spirocyclic ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethylbicyclo[2.2.1]heptanyl, and the like. Unless otherwise stated specifically in the specification, a cycloalkyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroaryl" refers to a 5- to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

The term "substituted" used herein means any of the groups described herein (e.g., alkyl, alkenyl, alkynyl, alkoxy, aryl, cycloalkyl, cycloalkenyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

Compounds

The present disclosure provides compounds that are prodrugs of tryptamines and relates scaffolds, for example N,N-dimethyltryptamine (DMT) as well as pharmaceutical compositions thereof.

DMT is metabolically unstable and is readily converted by monoamine oxidases (MAO's) to indoleacetic acid and N-oxidation metabolites resulting in poor oral bioavailability. In some embodiments, the compounds of the present disclosure allow for the controlled release of DMT. Advantages of compounds of the present disclosure may include increased metabolic stability, increased absorption, decreased maximal plasma concentrations of parent drug DMT over time, and less frequent dosing. In some embodiments, compounds of the present disclosure prevent or inhibit N-oxidation to promote oral bioavailability and increased exposure.

In some embodiments, compounds of the present disclosure comprise an enacarbil moiety. Without being bound by theory such compounds may for example, increase bioavailability by virtue of active transport of the prodrug in the small intestine by high-capacity nutrient transporters, including mono-carboxylate transporter-1 (MCT-1). DMT-enacarbil prodrugs may also reduce abuse potential by preventing absorption by snorting or insufflation.

In some embodiments, the present disclosure provides a compound of Formula (I):

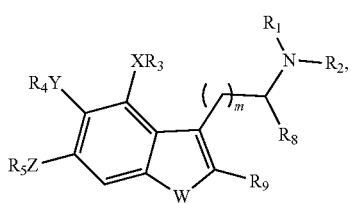
(I)

or a pharmaceutically acceptable salt thereof;
wherein,
$R_1$ and $R_2$ are independently hydrogen, alkyl, cycloalkyl, —or $R_1$ and $R_2$ together with the atoms to which they are attached form a heterocycle;
X, Y and Z are independently hydrogen, halogen, —O—, —S—, —$NR_A$—, or —(P=O)—$OR_A$(—OR'), wherein $R_A$ is hydrogen or alkyl;
R', $R_3$, $R_4$, $R_5$ and $R_6$ are independently absent, hydrogen, alkyl, —(C=O)-alkyl, —(C=O)$CHR_7$($NH_2$), —(C=O)($CH_2$)$_n$($NH_2$), —(C=O)CH($NH_2$)($CH_2$)$_n$($NH_2$), —(C=O)CH($NH_2$)($CH_2$)$_n$(NH)(C=NH)—$NH_2$, —(C=O)($CH_2$)$_n$(NH)(C=NH)—$NH_2$ or

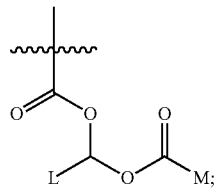

$R_7$ and $R_8$ are independently hydrogen or alkyl;
$R_9$ is hydrogen, alkyl, or halogen;
L and M are independently alkyl or aryl;
W is oxygen, sulfur or $NR_6$;
n is an integer from 2-7; and
m is an integer from 1-4,
wherein at least one of R', $R_3$, $R_4$, $R_5$ and $R_6$ is —(C=O)-alkyl, —(C=O)$CHR_7$($NH_2$), —(C=O)($CH_2$)$_n$($NH_2$), —(C=O)CH($NH_2$)($CH_2$)$_n$($NH_2$), —(C=O)($CH_2$)$_n$(NH)(C=NH)—$NH_2$ or

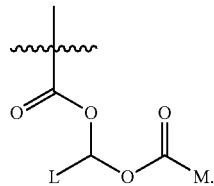

In some embodiments, provided herein is a compound of Formula (II)

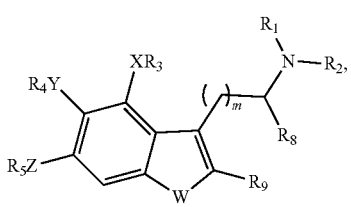
(II)

or a pharmaceutically acceptable salt thereof;
wherein,
$R_1$ and $R_2$ are independently hydrogen, alkyl, cycloalkyl, —or $R_1$ and $R_2$ together with the atoms to which they are attached form a heterocycle;
X, Y and Z are independently hydrogen, halogen, —O—, —S—, —$NR_A$—, or —(P=O)—$OR_A$(—OR'), wherein $R_A$ is hydrogen or alkyl;
R', $R_3$, $R_4$, $R_5$ and $R_6$ are independently absent, hydrogen, alkyl, —(C=O)-alkyl, —(C=O)$CHR_7$, —(C=O)($CH_2$)$_n$($NH_2$), —(C)CH($NH_2$)($CH_3$), —(C=O)CH($NH_2$), ($CH_2$)$_n$(NH)(C=NH), or —(C=O)($CH_2$)$_n$(NH)(C=NH)—$NH_2$;
$R_7$ and $R_8$ are independently hydrogen or alkyl;
$R_9$ is hydrogen, alkyl, or halogen;
L and M are independently alkyl or aryl;
W is oxygen, sulfur or $NR_6$;
n is an integer from 2-7; and
m is an integer from 1-4,
wherein at least one of R', $R_3$, $R_4$, and $R_5$ and $R_6$ is —(C=O)-alkyl, —(C=O)$CHR_7$($NH_2$), —(C=O)($CH_2$)$_n$($NH_2$), —(C=O)CH($NH_2$)($CH_2$)$_n$($NH_2$), —(C=O)($CH_2$)$_n$(NH)(C=NH)—$NH_2$ or

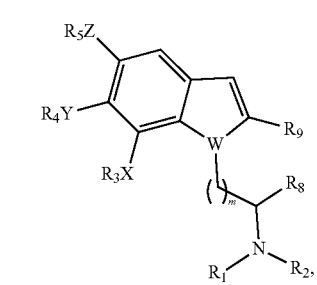

In some embodiments, $R_9$ is a halogen. In some embodiments, $R_9$ is bromo.

In some embodiments, provided herein is a compound of Formula (III):

(III)

or a pharmaceutically acceptable salt thereof;
wherein,
R₁ and R₂ are independently hydrogen, alkyl, cycloalkyl, —or R₁ and R₂ together with the atoms to which they are attached form a heterocycle;
X, Y and Z are independently hydrogen, halogen, —O—, —S—, —NR$_A$—, —O(P=O)—OR$_A$(—OR'), or —(P=O)—OR$_A$(—OR'), wherein R$_A$ is hydrogen or alkyl,
R', R₃, R₄, and R₅ are independently absent, hydrogen, alkyl, —(C=O)-alkyl, —(C=O)CHR₇(NH₂), —(C=O)(CH₂)$_n$(NH₂), —(C=O)CH(NH₂)(CH₂)$_n$(NH₂), —(C=O)CH(NH₂)(CH₂)$_n$(NH)(C=NH)—NH₂, —(C=O)(CH₂)$_n$(NH)(C=NH)—NH₂ or

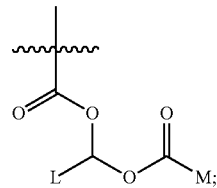

R₇ and R₈ are independently hydrogen or alkyl;
R₉ is hydrogen, alkyl, or halogen;
L and M are independently alkyl or aryl;
n is an integer from 2-7; and
m is an integer from 1-4,
wherein at least one of R', R₃, R₄, and R₅ is —(C=O)-alkyl, —(C=O)CHR₇(NH₂), —(C=O)(CH₂)$_n$(NH₂), —(C=O)CH(NH₂)(CH₂)$_n$(NH₂), —(C=O)(CH₂)$_n$(NH)(C=NH)—NH₂ or

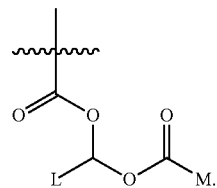

In some embodiments of the compounds of Formula (I), Formula (II), or Formula (III), R₁ and R₂ are independently hydrogen, alkyl, or cycloalkyl, —or R₁ and R₂ together with the atoms to which they are attached form a heterocycle.

In some embodiments of the compounds of Formula (I), Formula (II), or Formula (III), R₁ and R₂ are independently hydrogen, alkyl, or cycloalkyl.

In some embodiments of the compounds of Formula (I), Formula (II), or Formula (III), R₁ and R₂ together with the atoms to which they are attached form a heterocycle.

In some embodiments of the compounds of Formula (I), Formula (II), or Formula (III), R₁ and R₂ are independently hydrogen or $C_1$-$C_6$ alkyl.

In some embodiments of the compounds of Formula (I), Formula (II), or Formula (III), R₁ and R₂ are independently $C_1$-$C_6$ alkyl.

In some embodiments of the compounds of Formula (I), Formula (II), or Formula (III), R₁ and R₂ are independently methyl, ethyl, propyl, and isopropyl.

In some embodiments of the compounds of Formula (I), Formula (II), or Formula (III), R₁ and R₂ are methyl.

In some embodiments of the compounds of Formula (I), Formula (II), or Formula (III), X, Y and Z are independently hydrogen, halogen, —O—, —S—, —NR$_A$—, —O(P=O)—OR$_A$(—OR'), or —(P=O)—OR$_A$(—OR').

In some embodiments of the compounds of Formula (I), Formula (II), or Formula (III), X, Y and Z are H.

In some embodiments of the compounds of Formula (I), Formula (II), or Formula (III), two of X, Y and Z are hydrogen.

In some embodiments of the compounds of Formula (I), Formula (II), or Formula (III), two of X, Y and Z are hydrogen and the non-hydrogen X, Y or Z is —O—, —S—, —NR$_A$—, —O(P=O)—OR$_A$(—OR'), or —(P=O)—OR$_A$(—OR'), wherein R$_A$ is hydrogen or alkyl.

In some embodiments of the compounds of Formula (I), Formula (II), or Formula (III), X and Y are hydrogen; and Z is —O—, —S—, —NR$_A$—, —O(P=O)—OR$_A$(—OR'), or —(P=O)—OR$_A$(—OR'), wherein R$_A$ is hydrogen or alkyl.

In some embodiments of the compounds of Formula (I), Formula (II), or Formula (III), X and Z are hydrogen; and Y is —O—, —S—, —NR$_A$—, —O(P=O)—OR$_A$(—OR'), or —(P=O)—OR$_A$(—OR'), wherein R$_A$ is hydrogen or alkyl.

In some embodiments of the compounds of Formula (I), Formula (II), or Formula (III), Y and Z are hydrogen; and X is —O—, —S—, —NR$_A$—, —O(P=O)—OR$_A$(—OR'), or —(P=O)—OR$_A$(—OR'), wherein R$_A$ is hydrogen or alkyl.

In some embodiments of the compounds of Formula (I), Formula (II), or Formula (III), at least one of X, Y, or Z is —O(P=O)—OR$_A$(—OR').

In some embodiments of the compounds of Formula (I), Formula (II), or Formula (III), X is —O(P=O)—OR$_A$(—OR') and R₃ is absent.

In some embodiments of the compounds of Formula (I), Formula (II), or Formula (III), Y is —O(P=O)—OR$_A$(—OR') and R₄ is absent.

In some embodiments of the compounds of Formula (I), Formula (II), or Formula (III), Z is —O(P=O)—OR$_A$(—OR') and R₅ is absent.

In some embodiments of the compounds of Formula (I), Formula (II), or Formula (III), R' is hydrogen or alkyl.

In some embodiments of the compounds of Formula (I), Formula (II), or Formula (III), R$_A$ is hydrogen or alkyl.

In some embodiments of the compounds of Formula (I) or Formula (II), R', R₃, R₄, R₅ and R₆ are independently absent, hydrogen, alkyl, —(C=O)-alkyl, —(C=O)CHR₇(NH₂), —(C=O)(CH₂)$_n$(NH₂), —(C=O)CH(NH₂)(CH₂)$_n$(NH₂), —(C=O)CH(NH₂)(CH₂)$_n$(NH)(C=NH)—NH₂, —(C=O)(CH₂)$_n$(NH)(C=NH)—NH₂ or

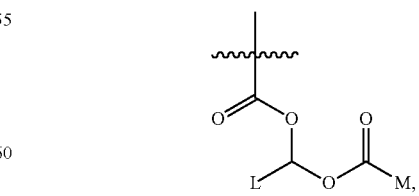

wherein at least one of R', R₃, R₄, R₅ and R₆ is —(C=O)-alkyl, —(C=O)CHR₇(NH₂), —(C=O)(CH₂)$_n$(NH₂), —(C=O)CH(NH₂)(CH₂)$_n$(NH₂), —(C=O)(CH₂)$_n$(NH)(C=NH)NH₂ or

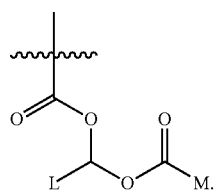

In some embodiments of the compounds of Formula (III), R', R$_3$, R$_4$, and R$_5$ are independently absent, hydrogen, alkyl, —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)CH(NH$_2$)(CH$_2$)$_n$(NH)(C=NH)—NH$_2$, —(C=O)(CH$_2$)$_n$(NH)(C=NH)—NH$_2$ or

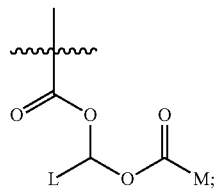

wherein at least one of R', R$_3$, R$_4$, and R$_5$ is —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

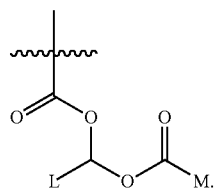

In some embodiments of the compounds of Formula (I), Formula (II), or Formula (III), R' is absent, hydrogen, alkyl, —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)CH(NH$_2$)(CH$_2$)$_n$(NH)(C=NH)—NH$_2$, —(C=O)(CH$_2$)$_n$(NH)(C=NH)—NH$_2$ or

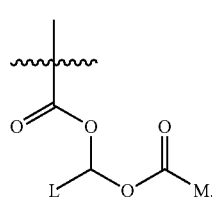

In some embodiments of the compounds of Formula (I), Formula (II), or Formula (III), R' is hydrogen or alkyl.

In some embodiments of the compounds of Formula (I), Formula (II), or Formula (III), R$_3$ is: —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

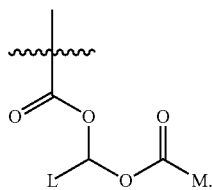

In some embodiments of the compounds of Formula (I), Formula (II), or Formula (III), R$_4$ is: —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

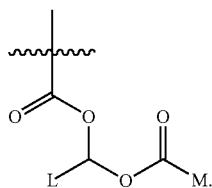

In some embodiments of the compounds of Formula (I), Formula (II), or Formula (III), R$_5$ is: —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

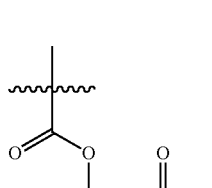

In some embodiments of the compounds of Formula (I), R$_6$ is: —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

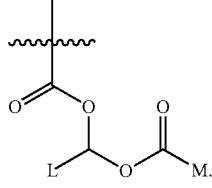

In some embodiments of the compounds of Formula (I), X, Y and Z are H; W is NR$_6$; and R$_6$ is —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

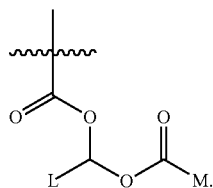

In some embodiments of the compounds of Formula (I), at least one of R', $R_3$, $R_4$, $R_5$ and $R_6$ is —(C=O)($CH_2$)$_n$($NH_2$) and n is 3.

In some embodiments of the compounds of Formula (I), at least one of R', $R_0$, $R_4$, $R_5$ and $R_6$ is —(C=O)CH($NH_2$)($CH_2$)$_n$($NH_2$), and n is 4.

In some embodiments of the compounds of Formula (I), at least one of R', $R_3$, $R_4$, $R_5$ and $R_6$ is —(C=O)($CH_2$)$_n$(NH)(C=NH)—$NH_2$ and n is 3.

In some embodiments of the compounds of Formula (I), at least one of R', $R_3$, $R_4$, $R_5$ and $R_6$ is —(C=O)CH(NH)($CH_2$)$_n$(C=NH)—$NH_2$ and n is 2.

In some embodiments of the compounds of Formula (I), at least one of R', $R_3$, $R_4$, $R_5$ and $R_6$ is

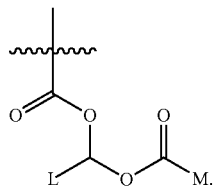

In some embodiments of the compounds of Formula (III), at least one of R', $R_3$, $R_4$, and $R_5$ is —(C=O)($CH_2$)$_n$($NH_2$) and n is 3.

In some embodiments of the compounds of Formula (III), at least one of R', $R_3$, $R_4$, and $R_5$ is —(C=O)CH($NH_2$)($CH_2$)$_n$($NH_2$) and n is 4.

In some embodiments of the compounds of Formula (III), at least one of R', $R_3$, $R_4$, and $R_5$ is —(C=O)($CH_2$)$_n$(NH)(C=NH)—$NH_2$ and n is 3.

In some embodiments of Formula (III), at least one of R', $R_3$, $R_4$, and $R_5$ is —(C=O)CH($NH_2$)($CH_2$)$_n$(NH)(C=NH)—$NH_2$ and n is 2.

In some embodiments of Formula (III), at least one of R', $R_3$, $R_4$, and $R_5$ is

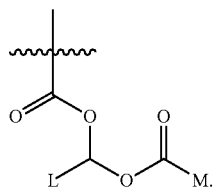

In some embodiments of the compounds of Formula (I), Formula (II), or Formula (III), L and M are independently alkyl or aryl.

In some embodiments of the compounds of Formula (I), Formula (II), or Formula (III), L is alkyl and M is alkyl or aryl.

In some embodiments of the compounds of Formula (I), Formula (II), or Formula (III), L is methyl or isopropyl and M is alkyl or aryl.

In some embodiments of the compounds of Formula (I) or Formula (II), W is oxygen, sulfur or $NR_6$;

In some embodiments of the compounds of Formula (I) or Formula (II), W is $NR_6$ and $R_6$ is hydrogen or alkyl.

In some embodiments of the compounds of Formula (I) or Formula (II), $R_7$, $R_8$, and $R_9$ are independently hydrogen or alkyl.

In some embodiments of the compounds of Formula (III), $R_8$, and $R_9$ are independently hydrogen or alkyl.

In some embodiments of the compounds of Formula (I), Formula (II), or Formula (III), $R_8$ is hydrogen.

In some embodiments of the compounds of Formula (I), Formula (II), or Formula (III), $R_8$ is alkyl.

In some embodiments of the compounds of Formula (I), Formula (II), or Formula (III), $R_8$ is $C_1$-$C_6$alkyl.

In some embodiments of the compounds of Formula (I), Formula (II), or Formula (III), $R_9$ is hydrogen, halogen, or alkyl.

In some embodiments of the compounds of Formula (I), Formula (II), or Formula (III), $R_9$ is hydrogen.

In some embodiments of the compounds of Formula (I), Formula (II), or Formula (III), $R_9$ is alkyl.

In some embodiments of the compounds of Formula (I), Formula (II), or Formula (III), $R_9$ is $C_1$-$C_6$ alkyl.

In some embodiments of the compounds of Formula (I), Formula (II), or Formula (III), $R_9$ is halogen. In some embodiments, $R_9$ is —F, —Cl, —Br, or —I. In some embodiments, $R_9$ is —Cl, —Br, or —I. In some embodiments, $R_9$ is —Cl or —Br. In some embodiments, $R_9$ is —F. In some embodiments, $R_9$ is —Cl. In some embodiments, $R_9$ is —Br. In some embodiments, $R_9$ is —I.

In some embodiments of the compounds of Formula (I) or Formula (II), $R_7$ and $R_8$ are independently hydrogen or $C_1$-$C_8$ alkyl optionally substituted with 1-3 groups independently selected from hydroxyl, thiol and halogen.

In some embodiments of the compounds of Formula (III), $R_8$ is hydrogen or $C_1$-$C_8$ alkyl optionally substituted with 1-3 groups independently selected from hydroxyl, thiol and halogen.

In some embodiments of the compounds of Formula (I), Formula (II), or Formula (III), $R_9$ is hydrogen, halogen, or $C_1$-$C_8$ alkyl optionally substituted with 1-3 groups independently selected from hydroxyl, thiol and halogen.

In some embodiments of the compounds of Formula (I) or Formula (II), $R_7$, $R_8$ and $R_9$ are independently hydrogen or $C_1$-$C_8$ alkyl optionally substituted with 1-3 groups independently selected from hydroxyl, thiol and halogen.

In some embodiments of the compounds of Formula (III), $R_8$ and $R_9$ are independently hydrogen or $C_1$-$C_8$ alkyl optionally substituted with 1-3 groups independently selected from hydroxyl, thiol and halogen.

In some embodiments of the compounds of Formula (I), Formula (II), or Formula (III), n is an integer from 2-7 (i.e. 2, 3, 4, 5, 6, or 7). In some embodiments n is 2. In some embodiments, n is 3. In some embodiments, n is 4. In some embodiments, n is 5. In some embodiments, n is 6. In some embodiments, n is 7.

In some embodiments of the compounds of Formula (I), Formula (II), or Formula (III), m is an integer from 1-4 (i.e. 1, 2, 3, or 4). In some embodiments, m is 1. In some embodiments, m is 2. In some embodiments, m is 3. In some embodiments, m is 4.

In some embodiments of the compounds of Formula (I), the compound is of Formula (IV):

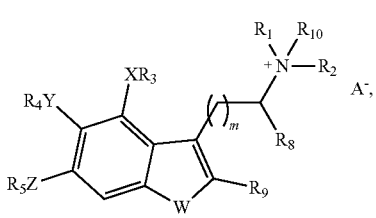
(IV)

wherein $R_{10}$ is —(C═O)-alkyl, —(C═O)CHR$_7$(NH$_2$), —(C═O)(CH$_2$)$_n$(NH$_2$), —(C═O)CH(NH$_2$)(CH$_2$)$_n$(NH$_2$), —(C═O)(CH$_2$)$_n$(NH)(C═NH)—NH$_2$ or

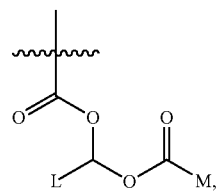

A is a pharmaceutically acceptable anion, and wherein $R_1$, $R_2$, $R_3$, $R_4$, $R_5$, $R_8$, $R_9$, X, Y, Z, W, and m are defined herein.

In some embodiments, the compound of Formula (I) is a compound of Formula (V):

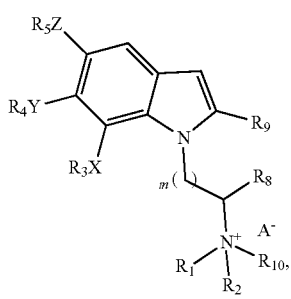
(V)

wherein $R_{10}$ is —(C═O)-alkyl, —(C═O)CHR$_7$(NH$_2$), —(C═O)(CH$_2$)$_n$(NH$_2$), —(C═O)CH(NH$_2$)(CH$_2$)$_n$(NH$_2$)), —(C═O)CH(NH$_2$)(CH$_2$)$_n$(NH)(C═NH)—NH$_2$, —(C═O)(CH$_2$)$_n$(NH)(C═NH)—NH$_2$ or

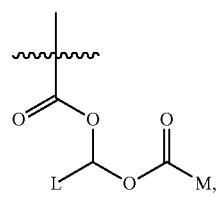

A is a pharmaceutically acceptable anion, and wherein $R_1$, $R_2$, $R_3$, $R_4$, $R_5$, $R_8$, $R_9$, X, Y, Z, and m are defined herein.

In some embodiments, the present disclosure provides compounds of Formula (VI):

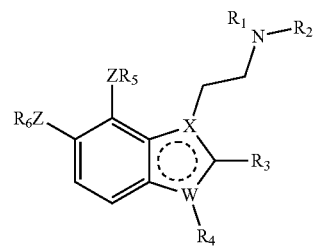
(VI)

wherein $R_1$, $R_2$, $R_3$, $R_4$, and $R_5$ are as defined herein,

X is carbon or nitrogen;

W is carbon, oxygen, or nitrogen; and

Z is hydrogen, deuterium, or oxygen.

In some embodiments, the compound of Formula (VII) is:

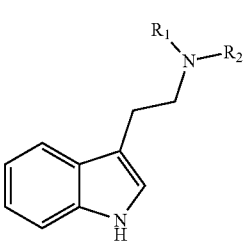
(VII)

In some embodiments, the compound of Formula (VI) or (VII) is:

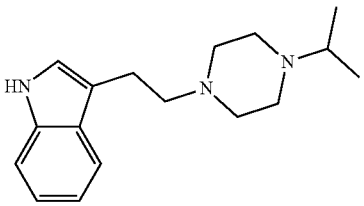
1-2-1

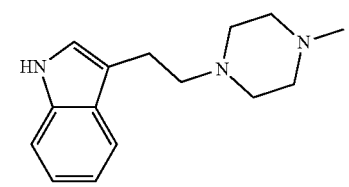
1-2-2

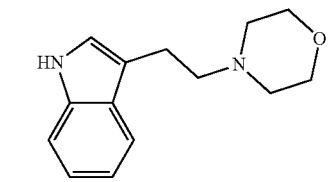
1-2-3

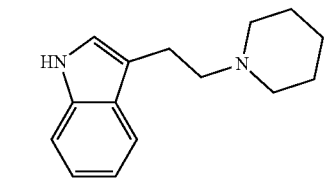
1-2-4

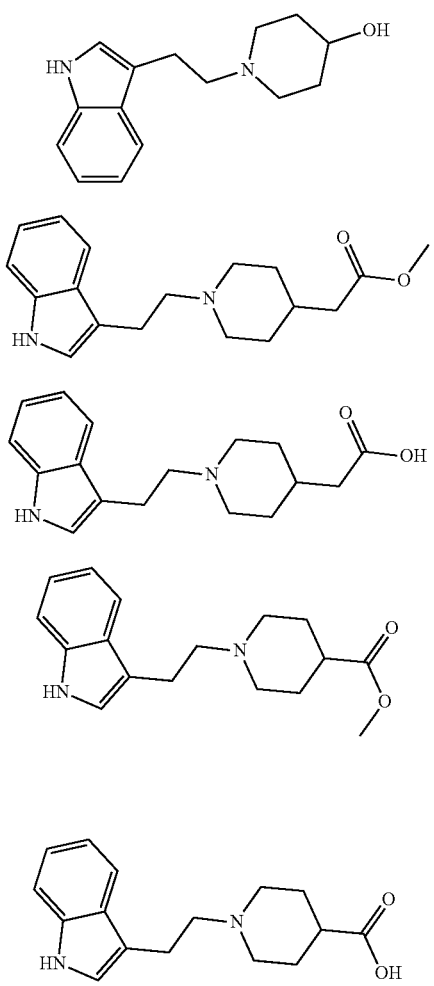
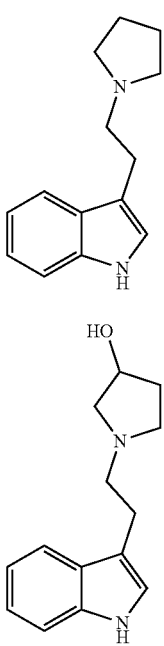
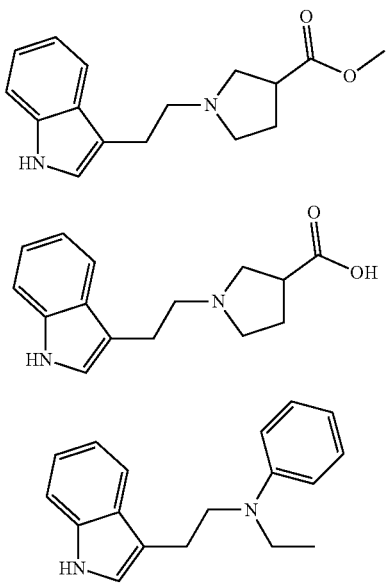
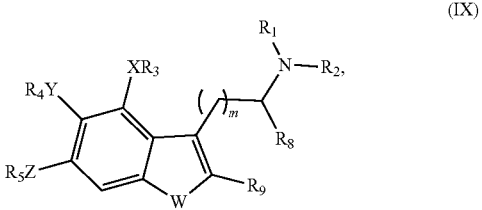

In some embodiments, the present disclosure provides compounds of Formula (VIII):

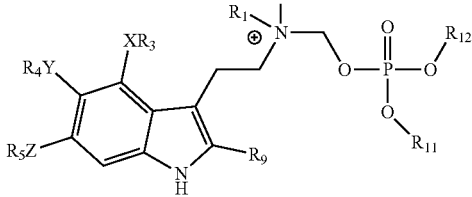

(VIII)

wherein $R_1$, $R_2$, $R_3$, $R_4$, $R_5$, and $R_9$, are as defined herein, $R_{11}$ and $R_{12}$ are independently a pharmaceutically acceptable salt, hydrogen, deuterium, alkyl, substituted alkyl, cycloalkyl, —or $R_{11}$ and $R_{12}$ together with the atoms to which they are attached form an alkyl, cycloalkyl, heterocycles and are ether, hemiaminal ketal and amino acid.

In some embodiments of the compounds of Formula (VIII), $R_{11}$ and $R_{12}$ together with the atoms to which they are attached form a heterocycle.

In some embodiments of the compounds of Formula (VIII), the pharmaceutically acceptable salt is $Na^+$, $K^+$, or $NH_4^+$.

In some embodiments, provided herein is a compound of Formula (IX):

(IX)

or a pharmaceutically acceptable salt thereof;
wherein,
$R_1$ and $R_2$ are each independently hydrogen, alkyl, —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)CH(NH$_2$)(CH$_2$)$_n$(NH)(C=NH)—NH$_2$, —(C=O)(CH$_2$)$_n$(NH)(C=NH)—NH$_2$ or

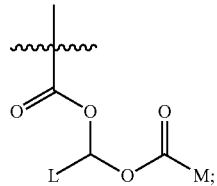

X, Y and Z are each independently hydrogen, halogen, —O—, —S—, —NR$_A$—, or —O(P=O)—OR$_A$(—OR'), wherein R' and R$_A$ is hydrogen or alkyl;
$R_3$, $R_4$, $R_5$ and $R_6$ are each independently absent, hydrogen, or alkyl;
$R_7$ and $R_8$ are each independently hydrogen or alkyl;
$R_9$ is hydrogen, alkyl, or halogen;
L and M are each independently alkyl or aryl;
W is oxygen, sulfur or NR$_6$;
n is an integer from 2-7; and
m is an integer from 1-4,
wherein at least one of $R_1$ and $R_2$ is —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)CH(NH$_2$)(CH$_2$)$_n$(NH)(C=NH)—NH$_2$, —(C=O)(CH$_2$)$_n$(NH)(C=NH)—NH$_2$ or

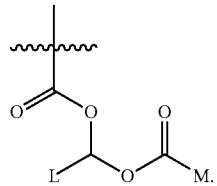

In some embodiments of the compounds of Formula (IX), X, Y and Z are each independently hydrogen, halogen, —O—, —S—, —NR$_A$—, or —O(P=O)—OR$_A$(—OR').

In some embodiments of the compounds of Formula (IX), X, Y and Z are hydrogen.

In some embodiments of the compounds of Formula (IX), two of X, Y and Z are hydrogen.

In some embodiments of the compounds of Formula (IX), two of X, Y and Z are hydrogen and the non-hydrogen X, Y or Z is —O—, —S—, —NR$_A$—, or —O(P=O)—OR$_A$(—OR'), wherein R$_A$ is hydrogen or alkyl.

In some embodiments of the compounds of Formula (IX), X and Y are hydrogen; and Z is —O—, —S—, —NR$_A$—, or —O(P=O)—OR$_A$(—OR'), wherein R$_A$ is hydrogen or alkyl.

In some embodiments of the compounds of Formula (IX), X and Z are hydrogen; and Y is —O—, —S—, —NR$_A$—, or —O(P=O)—OR$_A$(—OR'), wherein R$_A$ is hydrogen or alkyl.

In some embodiments of the compounds of Formula (IX), Y and Z are hydrogen; and X is —O—, —S—, —NR$_A$—, or —O(P=O)—OR$_A$(—OR'), wherein R$_A$ is hydrogen or alkyl.

In some embodiments of the compounds of Formula (IX), at least one of X, Y, or Z is —O(P=O)—OR$_A$(—OR').

In some embodiments of the compounds of Formula (IX), X is —O(P=O)—OR$_A$(—OR') and $R_3$ is absent.

In some embodiments of the compounds of Formula (IX), Y is —O(P=O)—OR$_A$(—OR') and $R_4$ is absent.

In some embodiments of the compounds of Formula (IX), Z is —O(P=O)—OR$_A$(—OR') and $R_5$ is absent.

In some embodiments of the compounds of Formula (IX), R' is hydrogen or alkyl.

In some embodiments of the compounds of Formula (IX), R$_A$ is hydrogen or alkyl.

In some embodiments of the compounds of Formula (IX), $R_1$ and $R_2$ are each independently absent, hydrogen, alkyl, —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)CH(NH$_2$)(CH$_2$)$_n$(NH)(C=NH)—NH$_2$, —(C=O)(CH$_2$)$_n$(NH)(C=NH)—NH$_2$ or

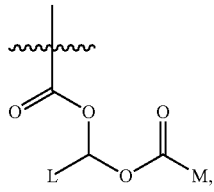

wherein at least one of $R_1$ and $R_2$ is —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

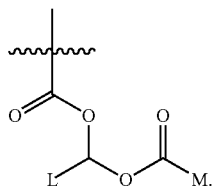

In some embodiments of the compounds of Formula (IX), $R_1$ is absent, hydrogen, alkyl, —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)CH(NH$_2$)(CH$_2$)$_n$(NH)(C=NH)—NH$_2$, —(C=O)(CH$_2$)$_n$(NH)(C=NH)—NH$_2$ or

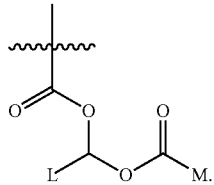

In some embodiments of the compounds of Formula (IX), $R_1$ is hydrogen or alkyl.

In some embodiments of the compounds of Formula (IX), $R_2$ is absent, hydrogen, alkyl, —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)CH(NH$_2$)(CH$_2$)$_n$(NH)(C=NH)—NH$_2$, —(C=O)(CH$_2$)$_n$(NH)(C=NH)—NH$_2$ or

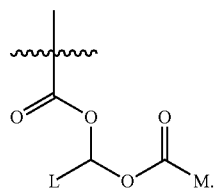

In some embodiments of the compounds of Formula (IX), $R_2$ is hydrogen or alkyl.

In some embodiments of the compounds of Formula (IX), at least one of $R_1$ and $R_2$ is —(C=O)(CH$_2$)$_n$(NH$_2$) and n is 3.

In some embodiments of the compounds of Formula (IX), at least one of $R_1$ and $R_2$ is —(C=O)CH(NH$_2$)(CH$_2$)$_n$(NH$_2$) and n is 4.

In some embodiments of the compounds of Formula (IX), at least one of $R_1$ and $R_2$ is —(C=O)(CH$_2$)$_n$(NH)(C=NH)—NH$_2$ and n is 3.

In some embodiments of the compounds of Formula (IX), at least one of $R_1$ and $R_2$ is —(C=O)CH(NH)(CH$_2$)$_n$(C=NH)—NH$_2$ and n is 2.

In some embodiments of the compounds of Formula (IX), at least one of $R_1$ and $R_2$ is —(C=O)-alkyl.

In some embodiments of the compounds of Formula (IX), at least one of $R_1$ and $R_2$ is

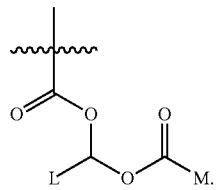

In some embodiments of the compounds of Formula (IX), at least one of $R_1$ and $R_2$ is —(C=O)CH(NH$_2$)(CH$_2$)$_n$(NH)(C=NH)—NH$_2$ and n is 4.

In some embodiments of the compounds of Formula (IX), at least one of $R_1$ and $R_2$ is —(C=O)CH(NH$_2$)(CH$_2$)$_n$(NH)(C=NH)—NH$_2$ and n is 3.

In some embodiments of the compounds of Formula (IX), L and M are each independently alkyl or aryl.

In some embodiments of the compounds of Formula (IX), L is alkyl and M is alkyl or aryl.

In some embodiments of the compounds of Formula (IX), L is methyl or isopropyl and M is alkyl or aryl.

In some embodiments, $R_3$ is hydrogen.
In some embodiments, $R_3$ is alkyl.
In some embodiments, $R_3$ is $C_1$-$C_6$ alkyl.
In some embodiments, $R_3$ is absent.
In some embodiments, $R_4$ is hydrogen.
In some embodiments, $R_4$ is alkyl.
In some embodiments, $R_4$ is $C_1$-$C_6$ alkyl.
In some embodiments, $R_4$ is absent.
In some embodiments, $R_5$ is hydrogen.
In some embodiments, $R_5$ is alkyl.
In some embodiments, $R_5$ is $C_1$-$C_6$ alkyl.
In some embodiments, $R_5$ is absent.

In some embodiments of the compounds of Formula (IX), W is oxygen, sulfur or $NR_6$.

In some embodiments of the compounds of Formula (IX), W is $NR_6$ and $R_6$ is hydrogen or alkyl.

In some embodiments of the compounds of Formula (IX), $R_7$, $R_8$, and $R_9$ are each independently hydrogen or alkyl.

In some embodiments of the compounds of Formula (IX), $R_8$ is hydrogen.

In some embodiments of the compounds of Formula (IX), $R_8$ is alkyl.

In some embodiments of the compounds of Formula (IX), $R_8$ is $C_1$-$C_6$ alkyl.

In some embodiments of the compounds of Formula (IX), $R_9$ is hydrogen, halogen, or alkyl.

In some embodiments of the compounds of Formula (IX), $R_9$ is hydrogen.

In some embodiments of the compounds of Formula (IX), $R_9$ is alkyl.

In some embodiments of the compounds of Formula (IX), $R_9$ is $C_1$-$C_6$ alkyl.

In some embodiments of the compounds of Formula (IX), $R_9$ is halogen. In some embodiments, $R_9$ is —F, —Cl, —Br, or —I. In some embodiments, $R_9$ is —Cl, —Br, or —I. In some embodiments, $R_9$ is —Cl or —Br. In some embodiments, $R_9$ is —F. In some embodiments, $R_9$ is —Cl. In some embodiments, $R_9$ is —Br. In some embodiments, $R_9$ is —I.

In some embodiments of the compounds of Formula (IX), $R_7$ and $R_8$ are each independently hydrogen or $C_1$-$C_8$ alkyl optionally substituted with 1-3 groups independently selected from hydroxyl, thiol and halogen.

In some embodiments of the compounds of Formula (IX), $R_9$ is hydrogen, halogen, or $C_1$-$C_8$ alkyl optionally substituted with 1-3 groups independently selected from hydroxyl, thiol and halogen.

In some embodiments of the compounds of Formula (IX), $R_7$, $R_8$ and $R_9$ are each independently hydrogen or $C_1$-$C_8$ alkyl optionally substituted with 1-3 groups independently selected from hydroxyl, thiol and halogen.

In some embodiments of the compounds of Formula (IX), n is an integer from 2-7 (i.e. 2, 3, 4, 5, 6, or 7). In some embodiments n is 2. In some embodiments, n is 3. In some embodiments, n is 4. In some embodiments, n is 5. In some embodiments, n is 6. In some embodiments, n is 7.

In some embodiments of the compounds of Formula (IX), m is an integer from 1-4 (i.e. 1, 2, 3, or 4). In some embodiments, m is 1. In some embodiments, m is 2. In some embodiments, m is 3. In some embodiments, m is 4.

In some embodiments, provided herein is a compound of Formula (X):

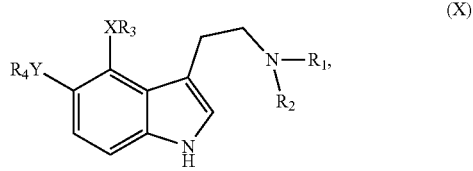

wherein
$R_1$ and $R_2$ together with the atoms to which they are attached form a heterocycle;
X and Y are each independently hydrogen, halogen, —O—, —S—, —NR$_A$—, or —O(P=O)—OR$_A$(—OR'), wherein $R_A$ is hydrogen or alkyl; and
R', $R_3$ and $R_4$ are each independently absent, hydrogen, alkyl, —(C=O)-alkyl, —(C=O)CHR$_7$(NH$_2$), —(C=O)(CH$_2$)$_n$(NH$_2$), —(C=O)CH(NH$_2$)(CH$_2$)$_n$ (NH$_2$), —(C=O)CH(NH$_2$) (CH$_2$)$_n$(NH)(C=NH)—NH$_2$, —(C=O)(CH$_2$)$_n$(NH)(C=NH)—NH$_2$ or

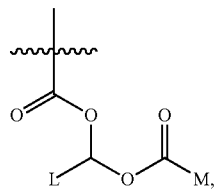

wherein at least one of R', R$_3$, and R$_4$ is —(C=O)-alkyl, —(C=O)CHR$_7$(NH$_2$), —(C=O)(CH$_2$)$_n$(NH$_2$), —(C=O)CH(NH$_2$)(CH$_2$)$_n$(NH$_2$), —(C=O)(CH$_2$)$_n$(NH)(C=NH)—NH$_2$ or

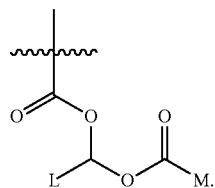

In some embodiments, provided herein is one or more compounds selected from Table 1.

In some embodiments, provided herein is one or more pharmaceutically acceptable salts of a compound selected from Table 1.

TABLE 1

| Compounds | |
|---|---|
| No. | Structure |
| 1-1 | [structure] |
| 1-2 | [structure] |

TABLE 1-continued

| Compounds | |
|---|---|
| No. | Structure |
| 1-3 | [structure] |
| 1-4 | [structure] |
| 1-5 | [structure] |
| 1-6 | [structure] |
| 1-7 | [structure] |

TABLE 1-continued
| No. | Structure |
|---|---|
| 1-8 | 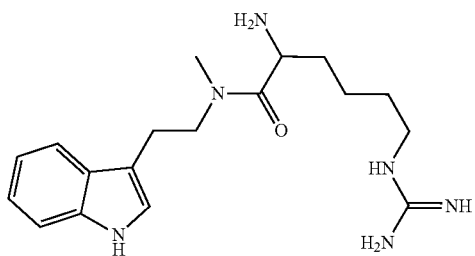 [SMILES: CN(CCc1c[nH]c2ccccc12)C(=O)C(N)CCCCNC(=N)N] |
| 1-9 | 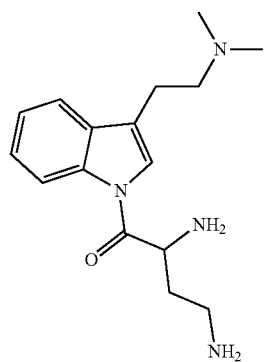 [SMILES: CN(C)CCc1cn(C(=O)C(N)CCN)c2ccccc12] |
| 1-10 | 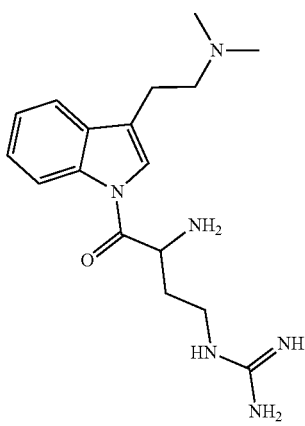 [SMILES: CN(C)CCc1cn(C(=O)C(N)CCNC(=N)N)c2ccccc12] |
| 1-11 | 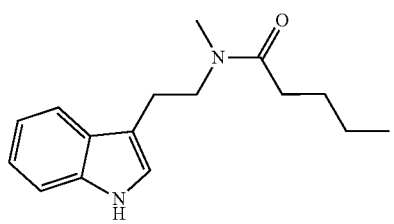 [SMILES: CCCCC(=O)N(C)CCc1c[nH]c2ccccc12] |
| 1-12 | 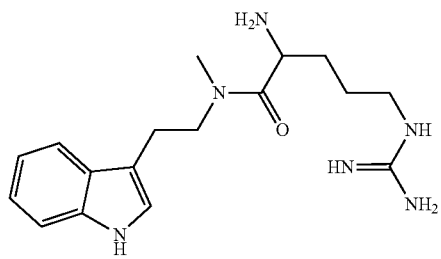 [SMILES: CN(CCc1c[nH]c2ccccc12)C(=O)C(N)CCCNC(=N)N] |
| 1-13 | 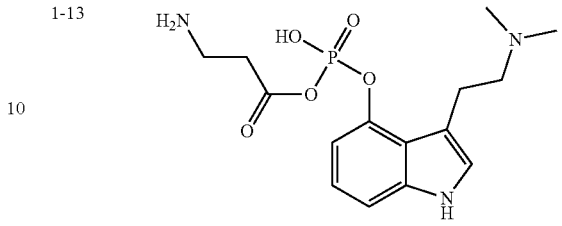 |
In some embodiments, provided herein is one or more compounds selected from Table 2.
In some embodiments, provided herein is one or more pharmaceutically acceptable salts of a compound selected from Table 2.
TABLE 2
| No. | Structure |
|---|---|
| 2-1 | 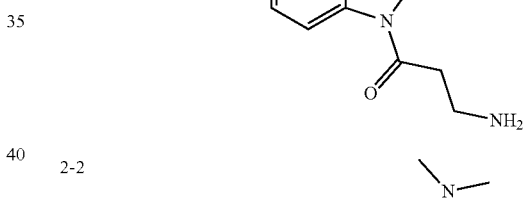 |
| 2-2 | 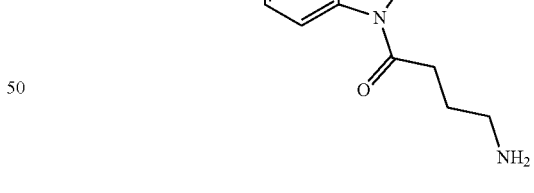 |
| 2-3 | 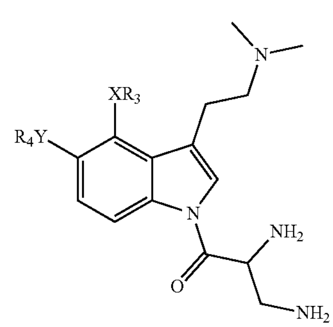 |

TABLE 2-continued

| No. | Structure |
|---|---|
| 2-4 | (structure) |
| 2-5 | (structure) |
| 2-6 | (structure) |
| 2-7 | (structure) |
| 2-8 | (structure) |
| 2-9 | (structure) |
| 2-10 | (structure) |
| 2-11 | (structure) |
| 2-12 | (structure) |
| 2-13 | (structure) |

In some embodiments of the compounds of Table 2, X and Y are hydrogen and $R_3$ and $R_4$ are absent.

In some embodiments of the compounds of Table 2, X is hydrogen, $R_3$ is absent, Y is O, and $R_4$ is hydrogen.

In some embodiments of the compounds of Table 2, X is hydrogen, $R_3$ is absent, Y is O, and $R_4$ is Me.

In some embodiments of the compounds of Table 2, X is hydrogen, $R_3$ is absent, Y is O, and $R_4$ is Ac.

In some embodiments of the compounds of Table 2, X is O, $R_3$ is hydrogen, Y is hydrogen, and $R_4$ is absent.

In some embodiments of the compounds of Table 2, X is O, $R_3$ is Me, Y is hydrogen, and $R_4$ is absent.

In some embodiments of the compounds of Table 2, X is O, $R_3$ is Ac, Y is hydrogen, and $R_4$ is absent. In some embodiments, provided herein is one or more compounds selected from Table 3.

In some embodiments, provided herein is one or more pharmaceutically acceptable salts of a compound selected from Table 3.

TABLE 3

| No. | Structure |
|---|---|
| 3-1 | (structure) |
| 3-2 | (structure) |
| 3-3 | (structure) |
| 3-4 | (structure) | wherein X, Y, $R_3$ and $R_4$ have the definitions provided herein.

In some embodiments of the compounds of Table 3, $R_3$ is absent, X is hydrogen, $R_4$ is absent, and Y is hydrogen.

In some embodiments of the compounds of Table 3, $R_3$ is absent, X is hydrogen, $R_4$ is hydrogen, and Y is —O—.

In some embodiments of the compounds of Table 3, $R_3$ is absent, X is hydrogen, $R_4$ is alkyl, and Y is —O—.

In some embodiments of the compounds of Table 3, $R_3$ is hydrogen, X is —O—, $R_4$ is absent hydrogen, and Y is hydrogen.

In some embodiments of the compounds of Table 3, $R_3$ is alkyl, X is —O—, $R_4$ is absent hydrogen, and Y is hydrogen.

In some embodiments of the compounds of Table 3, $R_3$ is absent, X is hydrogen, $R_4$ is absent, Y is —O(P=O)(OR$_A$)(OR'), $R_A$ is hydrogen or alkyl, and R' is hydrogen or alkyl.

In some embodiments of the compounds of Table 3, $R_3$ is absent, X is hydrogen, $R_4$ is absent, and Y is —O(P=O)(OH)(OH).

In some embodiments of the compounds of Table 3, $R_3$ is absent, X is —O(P=O)(OR$_A$)(OR'), $R_A$ is hydrogen or alkyl, R' is hydrogen or alkyl, $R_4$ is absent, and Y is hydrogen.

In some embodiments of the compounds of Table 3, $R_3$ is absent, X is —O(P=O)(OH)(OH), $R_4$ is absent, and Y is hydrogen.

In some embodiments, provided herein is one or more compounds selected from Table 4.

In some embodiments, provided herein is one or more pharmaceutically acceptable salts of a compound selected from Table 4.

TABLE 4

Compounds 1-2-1

(structure)

1-2-1

1-2-2

(structure)

1-2-2

1-2-3

(structure)

1-2-3

TABLE 4-continued
Compounds
1-2-4
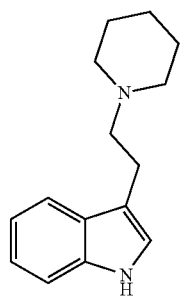 [SMILES: c1ccc2c(CCN3CCCCC3)c[nH]c2c1]
1-2-4
1-2-5
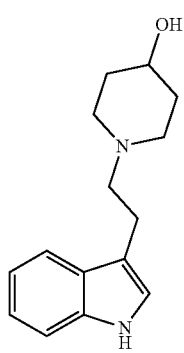 [SMILES: OC1CCN(CCc2c[nH]c3ccccc23)CC1]
1-2-5
1-2-6
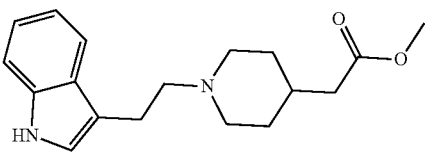 [SMILES: COC(=O)CC1CCN(CCc2c[nH]c3ccccc23)CC1]
1-2-6
1-2-7
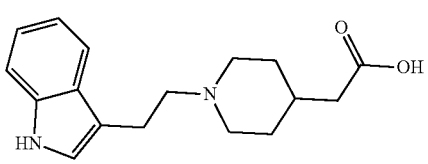 [SMILES: O=C(O)CC1CCN(CCc2c[nH]c3ccccc23)CC1]
1-2-7
1-2-8
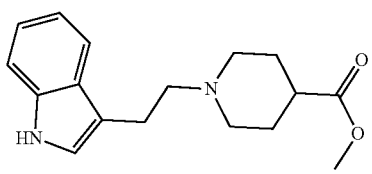 [SMILES: COC(=O)C1CCN(CCc2c[nH]c3ccccc23)CC1]
1-2-8
1-2-9
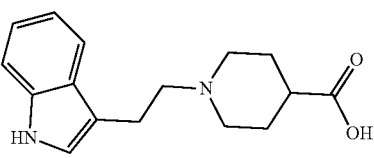 [SMILES: O=C(O)C1CCN(CCc2c[nH]c3ccccc23)CC1]
1-2-9
TABLE 4-continued
Compounds
1-2-10
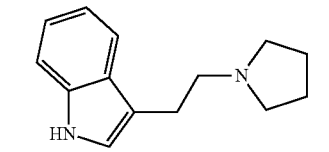
1-2-10
1-2-11
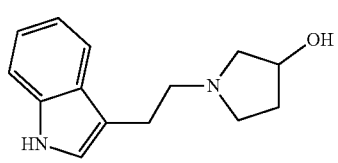 [SMILES: OC1CCN(CCc2c[nH]c3ccccc23)C1]
1-2-11
1-2-12
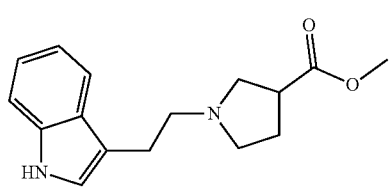 [SMILES: COC(=O)C1CCN(CCc2c[nH]c3ccccc23)C1]
1-2-12
1-2-13
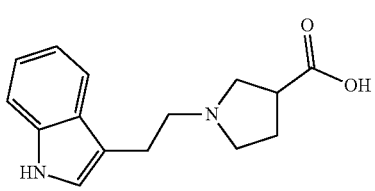 [SMILES: O=C(O)C1CCN(CCc2c[nH]c3ccccc23)C1]
1-2-13
1-2-14
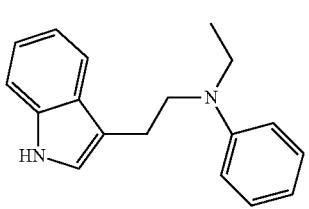 [SMILES: CCN(CCc1c[nH]c2ccccc12)c1ccccc1]
1-2-14
2-1-2
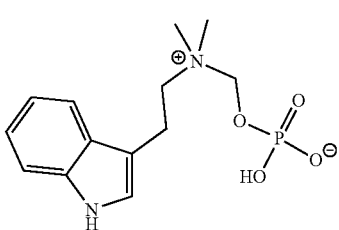 [SMILES: C[N+](C)(CCc1c[nH]c2ccccc12)COP(=O)([O-])O]
2-1-2
3-1-2
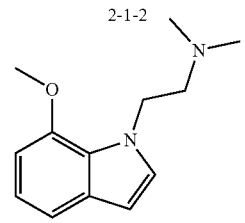
3-1-2

TABLE 4-continued

Compounds 3-1-3

3-1-4

4-1-1

4-1-2

4-1-3

4-1-4

5-1-1

5-1-2

5-1-3

5-1-4

TABLE 4-continued

Compounds 6-1-1

[Chemical structure of compound 6-1-1: N,N-dimethyltryptamine-like structure]

6-1-2

[Chemical structure of compound 6-1-2: tryptamine with quaternary ammonium bearing a phosphate ester group]

6-1-3

[Chemical structure of compound 6-1-3: tryptamine with quaternary ammonium bearing a hydroxymethyl group]

Compositions

In some embodiments of the present disclosure, a pharmaceutical composition comprises a therapeutically effective amounts of one or more compounds of the present disclosure (e.g., a compound of Formulas (I)-(X) or Compounds of Tables 1-4) or a pharmaceutically acceptable salt thereof and a pharmaceutically acceptable excipient.

The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Methods

In one aspect, the present disclosure provides methods of treating or preventing neurological disorders in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof to the subject.

In some embodiments, the neurological disorder is a mood disorder. In some embodiments, the mood disorder is clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, major depressive disorder, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with neuroendocrine diseases and disorders, neurodegenerative diseases and disorders (e.g., epilepsy), movement disorders, tremor (e.g., Parkinson's Disease), or women's health disorders or conditions. In some embodiments, the mood disorder is depression. In some embodiments, the mood disorder is treatment-resistant depression or major depressive disorder. In some embodiments, the mood disorder is major depressive disorder. In some embodiments, the mood disorder is treatment-resistant depression.

In some embodiments, the present disclosure provides methods of treating or preventing PTSD, mood disorders, general anxiety disorder, addictive disorders, and/or drug dependence in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof to the subject.

In some embodiments, the present disclosure provides methods of treating or preventing PTSD in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof to the subject.

In some embodiments, the methods include treating PTSD through induction and maintenance therapy by administering a compound disclosed herein, a pharmaceutically acceptable salt thereof, or a pharmaceutical composition thereof. In some embodiments, the compounds of the present disclosure are used for induction and maintenance therapy to treat PTSD with an improved safety profile when compared to treatment with the entactogenic, oneirophrenic or psychedelic compound (e.g., dimethyltryptamine or related compound, psilocybin, or MDMA) alone.

In some embodiments, the present disclosure provides methods of treating or preventing behavioral or mood disorders in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof to the subject. In some embodiments, the behavioral or mood disorder includes anxiety, such as social anxiety in autistic subjects (e.g., autistic adults) and anxiety related to life-threatening illnesses. In some embodiments, the behavioral or mood disorder includes stress (where moderation thereof is measured, e.g., by effects on amygdala responses). In some embodiments, the anxiety disorder is panic disorder, obsessive-compulsive disorder, and/or general anxiety disorder. In some embodiments, the subject suffers from a lack of motivation, attention, lack of accuracy in memory recall, speed of response, perseveration, and/or cognitive engagement. Further examples include depression (e.g., MDD or TRD), attention disorders, disorders of executive function and/or cognitive engagement, obsessive compulsive disorder, bipolar disorder, panic disorder, phobia, schizophrenia, psychopathy, antisocial personality disorder and/or neurocognitive disorders.

In some embodiments, the present disclosure provides methods for treating an addictive disorder in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof to the subject. In some embodiments, the addictive disorder is alcohol abuse, substance abuse, smoking, obesity, or mixtures thereof. In some embodiments, the disorder is an eating disorder (e.g., anorexia nervosa, bulimia, nervosa, binge eating disorder, etc.) or an auditory disorder.

In some embodiments, the present disclosure provides methods for treating an impulsive disorder in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof to the subject. In some embodiments, the impulsive disorder is attention deficit hyperactivity disorder (ADHD), attention deficit disorder (ADD), Tourette's syndrome, autism, or combinations thereof.

In some embodiments, the present disclosure provides methods for treating a compulsive disorder in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof to the subject. In some embodiments, the compulsive disorder is obsessive compulsive disorder (OCD), gambling, aberrant sexual behavior, or combinations thereof.

In some embodiments, the present disclosure provides methods for treating a personality disorder in a subject in need thereof, the methods comprising administering a therapeutically effective amount of a compound disclosed herein (e.g., a compound of Formulas (I)-(X) or Compounds of Tables 1-4), a pharmaceutically acceptable salt thereof, or a pharmaceutical composition thereof. In some embodiments, the personality disorder is conduct disorder, antisocial personality, aggressive behavior, or combinations thereof to the subject.

Examples

Compounds of the present disclosure can be synthesized using the following exemplary methods or other methods that are known to those skilled in the art.

General reaction conditions are provided, and reaction products can be purified by known methods including silica gel chromatography using various organic solvents such as hexane, dichloromethane, ethyl acetate, methanol and the like or preparative reverse phase high pressure liquid chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, as well as in Jerry March, *Advanced Organic Chemistry* 4$^{th}$ edition, John Wiley & Sons, publisher, New York, 1992 which are incorporated herein by reference in their entirety.

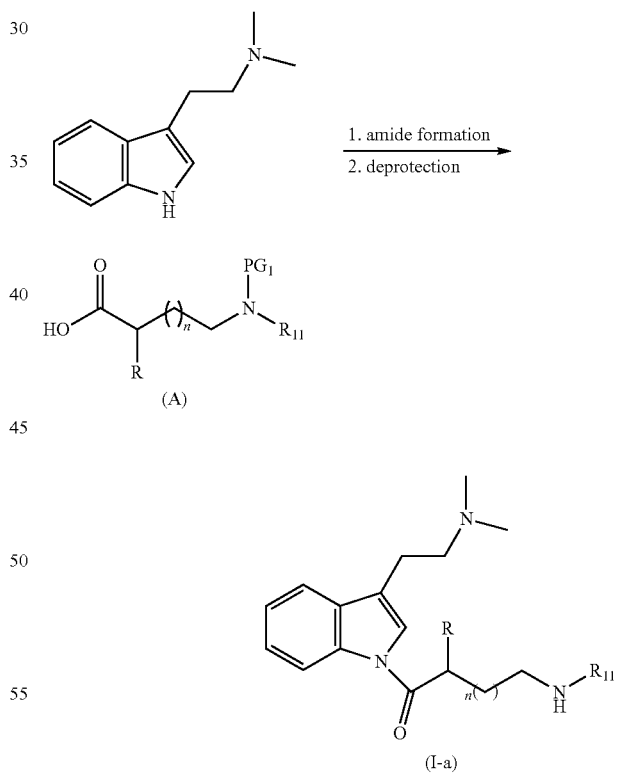

Scheme 1: Representative synthesis of compounds of the disclosure n = 1-3, R = H, NH$_2$ = R$_{11}$ = H, C = NH)NH$_2$ As shown in Scheme 1, 2-(1H-indol-3-yl)-N,N-dimethylethan-1-amine can be coupled with a carboxylic acid of Formula (A) where PG$_1$ is a protecting group (such as Boc) under amide coupling conditions (e.g., in the presence of 1,1'-carbonyldiimidazole (CDI), dimethylaminopyridine (DMAP) and a strong base, such as sodium hydride), followed by deprotection of the protecting group $PG_1$ (e.g., using TFA) to provide compounds of Formula (I-a).

Scheme 2: Representative synthesis of compounds of the disclosure

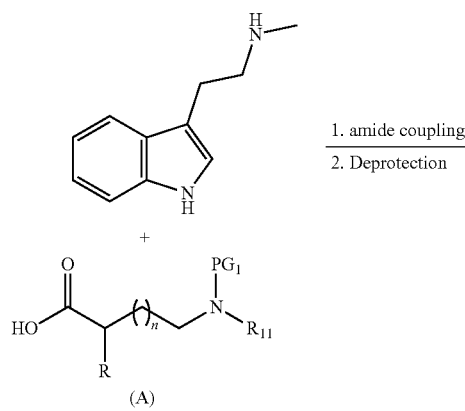

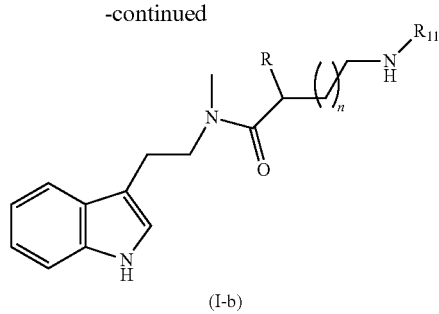

n = 1-3, R = H, $NH_2$ = $R_{11}$ = H, C=NH)$NH_2$    (I-b)

As shown in Scheme 2, 2-(1H-indol-3-yl)-N-methyl-ethan-1-amine can be reacted with a carboxylic acid of Formula (A) under amide coupling conditions (e.g., in the presence of CDI, DMAP and a base, such as a tertiary amine base like triethylamine) where $PG_1$ is a protecting group (such as Boc) followed by deprotection of the protecting group $PG_1$ (e.g., using TFA) to provide compounds of Formula (I-b).

Scheme 3: Representative synthesis of compounds of the disclosure

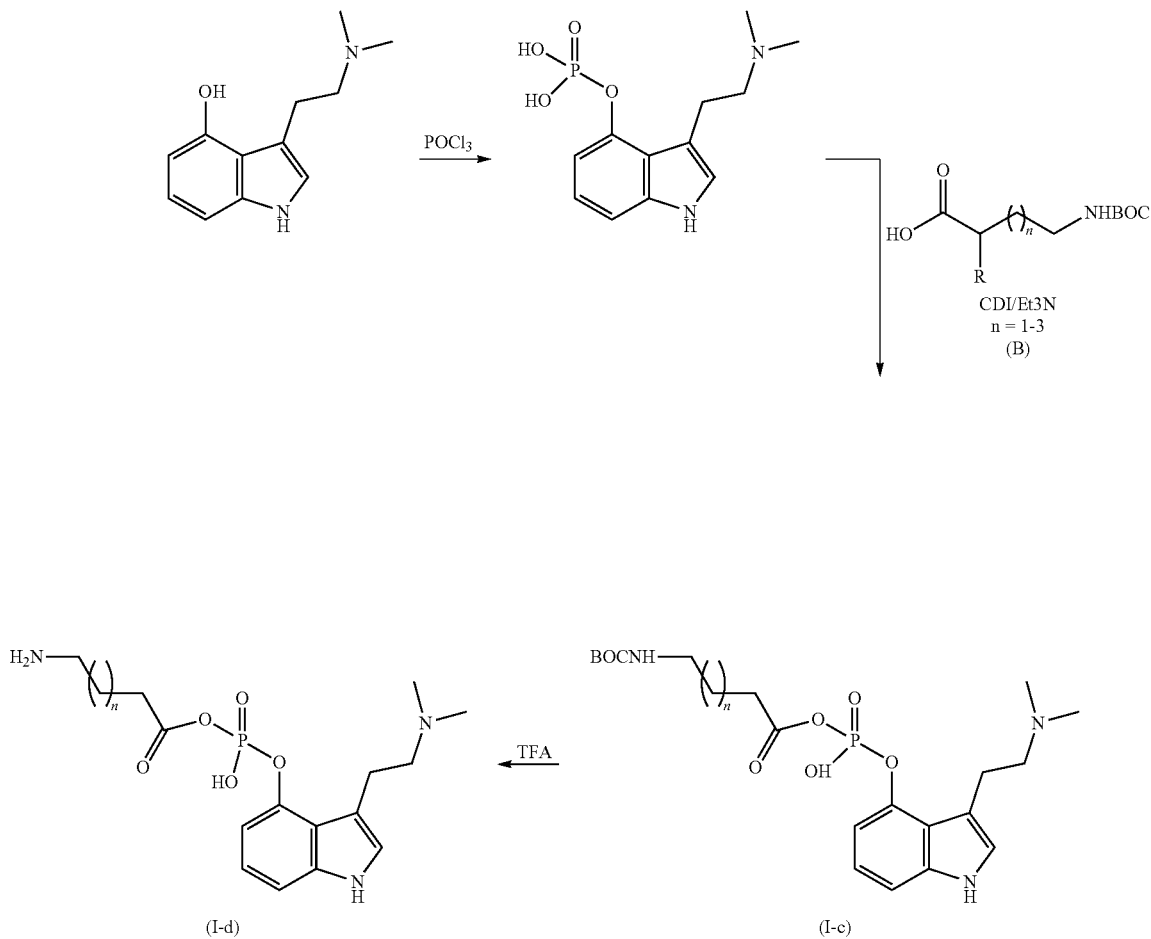

As shown in Scheme 3, 3-(2-(dimethylamino)ethyl)-1H-indol-4-ol can be converted into 3-(2-(dimethylamino)ethyl)-1H-indol-4-yl dihydrogen phosphate in the presence of POCl₃. 3-(2-(dimethylamino)ethyl)-1H-indol-4-yl dihydrogen phosphate can be reacted with a carboxylic acid of Formula (B) in the presence of CDI and a tertiary amine such as triethylamine to form a compound of Formula (I-c). Compounds of Formula (I-c) can be deprotected e.g., with TFA to provide compounds of Formula (I-d).

1. Synthesis of 1-2

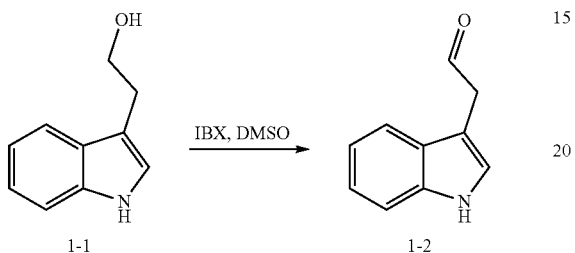

To a solution of tryptophol (6 g, 37.27 mmol, 1.0 equiv) in dimethyl sulfoxide (60 mL) was added 2-Iodoxybenzoic acid (12.5 g, 44.72 mmol, 1.2 equiv) at 40° C. under nitrogen atmosphere. The mixture solution was stirred for 2 h at 40° C. The reacting solution was diluted with 200 mL of dichloromethane, washed with 2×200 mL saturated sodium bicarbonate solution and 2×200 mL saturated aqueous sodium chloride respectively. The organic layer was dried over anhydrous sodium sulfate, filtered and concentrated under vacuum. The residue was applied onto a silica gel column with petroleum ether/ethyl acetate (3:1). 4 g (67%) of 1-2 was obtained as a yellow oil.

2. Synthesis of 1-2-1

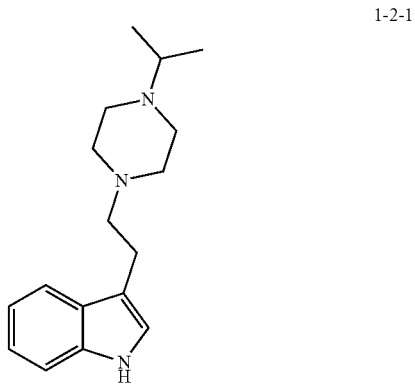 [SMILES: CC(C)N1CCN(CCc2c[nH]c3ccccc23)CC1]

To a solution of 1-2 (100 mg, 0.63 mmol, 1.00 equiv) and 1-Isopropylpiperazine (241.5 mg, 1.89 mmol, 3.00 equiv) in dichloromethane (1 mL) were added triethylamine (190.9 mg, 1.89 mmol, 3.00 equiv) and the solution of SnCl₄ in dichloromethane (1N, 0.32 mL, 0.5 equiv) at 25° C. The resulting mixture was stirred for 1 h at 25° C. under nitrogen atmosphere. Then sodium cyanoborohydride (58.6 mg, 0.95 mmol, 1.50 equiv) was added in portions. The mixture was stirred for 2 h at 25° C. The reaction was diluted with 20 mL of dichloromethane. The organic layer was washed with 2×20 mL saturated aqueous sodium chloride solution, dried over anhydrous sodium sulfate, filtered and concentrated under vacuum. The crude product was purified by Prep-HPLC for 2 times with the following condition: Column: XBridge Prep OBD C18 Column, 30*150 mm, 5 μm; Mobile Phase A: Water (10 mmol/L NH₄HCO₃+0.1% NH₃·H₂O), Mobile Phase B: ACN; Flow rate: 60 mL/min; Gradient: 22% B to 50% B in 9 min, 50% B; Wave Length: 254 nm; 4.6 mg (3%) of 1-2-1 was obtained as a brown solid. MS m/z [M+H]⁺ (ESI): 272.25. ¹H NMR (300 MHz, DMSO-d6) δ 10.76 (s, 1H), 7.51-7.49 (m, 1H), 7.34-7.32 (m, 1H), 7.14-6.97 (m, 3H), 2.83 (s, 2H), 2.58-2.46 (m, 11H), 0.97 (s, 6H).

3. Synthesis of 1-2-2

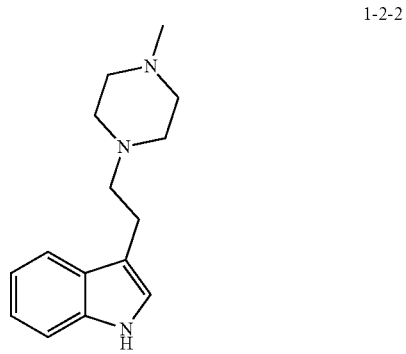 [SMILES: CN1CCN(CCc2c[nH]c3ccccc23)CC1]

In a similar manner described for 1-2-1, compound 1-2-2 was prepared from 100 mg of 1-2 and 189 mg of 1-methylpiperazine. 5.1 mg (3%) of 1-2-2 was obtained as a brown oil. MS m/z [M+H]⁺ (ESI): 244.10. ¹H NMR (300 MHz, DMSO-d6) δ 10.75 (s, 1H), 7.49 (d, J=7.5 Hz, 1H), 7.32 (d, J=8.1 Hz, 1H), 7.13 (s, 1H), 7.05 (t, J=7.5 Hz, 1H), 6.95 (t, J=7.4 Hz, 1H), 2.85-2.79 (m, 2H), 2.58-2.53 (m, 2H), 2.47-2.33 (m, 8H), 2.15 (s, 3H).

4. Synthesis of 1-2-3

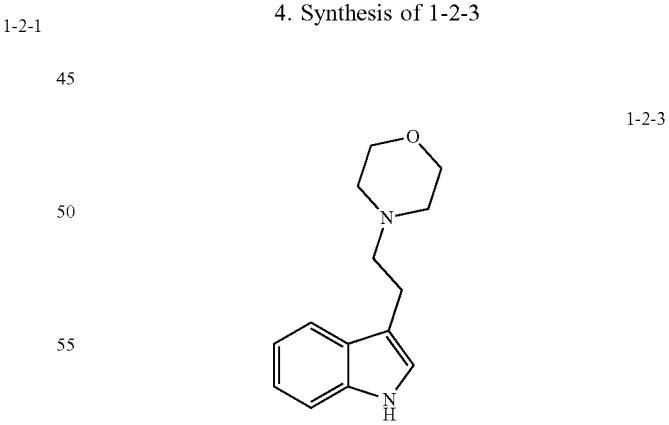

In a similar manner described for 1-2-1, compound 1-2-3 was prepared from 100 mg of 1-2 and 164.4 mg of morpholine. 25.5 mg (17%) of 1-2-3 was obtained as a brown solid. MS m/z [M+H]⁺ (ESI): 231.05. ¹H NMR (300 MHz, DMSO-d6) δ 10.77 (s, 1H), 7.50 (d, J=7.8 Hz, 1H), 7.32 (d, J=7.8 Hz, 1H), 7.15 (s, 1H), 7.07-6.94 (m, 2H), 3.60 (t, J=4.2 Hz, 4H), 2.84 (t, J=7.8 Hz, 2H), 2.54 (t, J=7.8 Hz, 2H), 2.47-2.45 (m, 4H).

Synthesis of 1-2-4

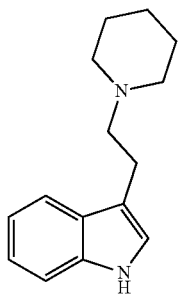

1-2-4

In a similar manner described for 1-2-1, compound 1-2-4 was prepared from 100 mg of 1-2 and 168.2 mg of piperidine. 3.4 mg (2%) of 1-2-4 was obtained as a brown solid. MS n/z [M+H]$^+$ (ESI): 229.20. $^1$H NMR (300 MHz, DMSO-d6) δ 10.75 (s, 1H), 7.49 (d, J=5.1 Hz, 1H), 7.32 (d, J=6.0 Hz, 1H), 7.12 (s, 1H), 7.04-6.95 (m, 2H), 2.82 (s, 2H), 2.55 (s, 2H), 2.42 (s, 4H), 1.51-1.40 (m, 6H).

Synthesis of 1-2-5

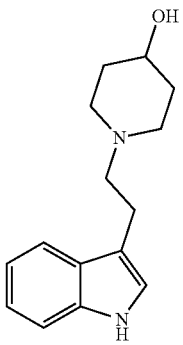

1-2-5

In a similar manner described for 1-2-1, compound 1-2-5 was prepared from 100 mg of 1-2 and 190.9 mg of 4-Hydroxypiperidine. 18.9 mg (12%) of 1-2-5 was obtained as a brown solid. MS m/z [M+H]$^+$ (ESI): 245.10. $^1$H NMR (300 MHz, DMSO-d6) δ 10.75 (s, 1H), 7.49 (d, J=7.8 Hz, 1H), 7.32 (d, J=7.8 Hz, 1H), 7.13-6.93 (m, 3H), 4.53 (s, 1H), 3.49-3.38 (m, 1H), 2.87-2.73 (m, 4H), 2.59-2.52 (m, 2H), 2.12-2.01 (m, 2H), 1.75-1.70 (m, 2H), 1.45-1.33 (m, 2H).

7. Synthesis of 1-2-6

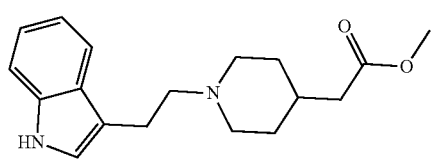

1-2-6

To a solution of methyl 4-piperidineacetate (296.7 mg, 1.89 mmol, 3.00 equiv) and acetic acid (0.1 mL) in methanol (1 mL) were added sodium cyanoborohydride (58.6 mg, 0.95 mmol, 1.50 equiv) at 0° C. Then 1-2 (100 mg, 0.63 mmol, 1.00 equiv) was added to the mixture dropwise at 0° C. The mixture was stirred at 25° C. for 2 h. The reaction was diluted with 20 mL of dichloromethane. The organic layer was washed with 2×20 mL saturated aqueous sodium chloride solution, dried over anhydrous sodium sulfate, filtered and concentrated under reduced pressure. The crude product was purified by Prep-HPLC with the following condition: Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 30% B to 58% B in 9 min, 58% B; Wavelength: 254 nm. 27.1 mg (14%) of 1-2-6 was obtained as a brown solid. MS m/z [M+H]$^+$ (ESI): 301.05. $^1$H NMR (300 MHz, DMSO-d6) δ 10.75 (s, 1H), 7.49 (d, J=7.8 Hz, 1H), 7.32 (d, J=8.1 Hz, 1H), 7.12 (d, J=1.8 Hz, 1H), 7.07-7.02 (m, 1H), 6.97-6.93 (m, 1H), 3.59 (s, 3H), 2.96-2.92 (m, 2H), 2.84-2.79 (m, 2H), 2.57-2.51 (m, 2H), 2.24 (d, J=6.6 Hz, 2H), 1.98-1.89 (m, 2H), 1.72-1.60 (m, 3H), 1.29-1.13 (m, 2H).

8. Synthesis of 1-2-7

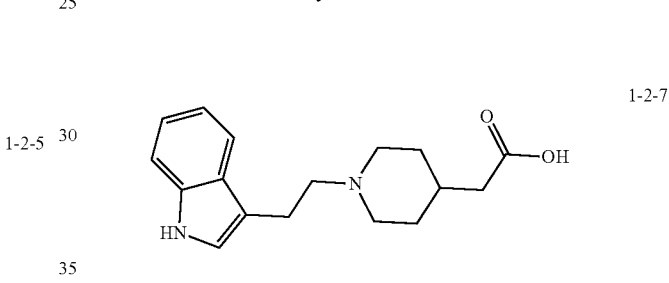

1-2-7

In a similar manner described for 1-2-1, compound 1-2-7 was prepared from 100 mg of 1-2 and 270.2 mg of piperidin-4-ylacetic acid. 7.8 mg (4%) of 1-2-7 was obtained as a white solid. MS m/z [M+H]$^+$ (ESI): 287.10. $^1$H NMR (300 MHz, DMSO-d6) δ 10.76 (s, 1H), 7.50 (d, J=7.5 Hz, 1H), 7.33 (d, J=7.4 Hz, 1H), 7.13-6.95 (m, 3H), 3.02-2.89 (m, 2H), 2.88-2.74 (m, 2H), 2.57-2.53 (m, 2H), 2.11 (s, 2H), 1.99-1.90 (m, 2H), 1.67-1.63 (m, 3H), 1.26-1.12 (m, 2H).

9. Synthesis of 1-2-8

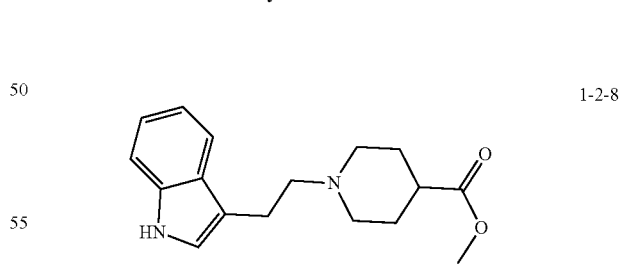

1-2-8

In a similar manner described for 1-2-7, compound 1-2-8 was prepared from 100 mg of 1-2 and 270.2 mg of methyl isonipecotate. 26.1 mg (14%) of 1-2-8 was obtained as a brown solid. MS m/z [M+H]$^+$ (ESI): 287.05. $^1$H NMR (300 MHz, DMSO-d6) 310.76 (s, 1H), 7.49 (d, J=7.8 Hz, 1H), 7.34-7.29 (m, 1H), 7.13 (d, J=2.1 Hz, 1H), 7.07-7.02 (m, 1H), 6.98-6.93 (m, 1H), 3.60 (s, 3H), 2.94-2.89 (m, 2H), 2.85-2.80 (m, 2H), 2.58-2.53 (m, 2H), 2.38-2.26 (m, 1H), 2.09-1.99 (m, 2H), 1.86-1.77 (m, 2H), 1.64-1.51 (m, 2H).

10. Synthesis of 1-2-9

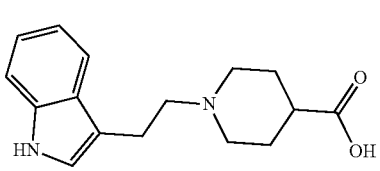

1-2-9

In a similar manner described for 1-2-1, compound 1-2-9 was prepared from 100 mg of 1-2 and 243.8 mg of isonipecotic acid. 4.3 mg (2%) of 1-2-9 was obtained as a white solid. MS i/z [M+H]⁺ (ESI): 273.10. ¹H NMR (300 MHz, DMSO-d6) δ 10.75 (s, 1H), 7.49 (d, J=7.2 Hz, 1H), 7.31 (d, J=7.5 Hz, 1H), 7.13 (s, 1H), 7.09-6.90 (m, 2H), 2.95-2.78 (m, 4H), 2.58-2.53 (m, 2H), 2.22-1.96 (m, 3H), 1.82-1.77 (m, 2H), 1.61-1.48 (m, 2H).

11. Synthesis of 1-2-10

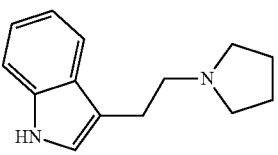

1-2-10

In a similar manner described for 1-2-1, compound 1-2-10 was prepared from 100 mg of 1-2 and 134.2 mg of pyrrolidine. 8.0 mg (6%) of 1-2-10 was obtained as a brown solid. MS m/z [M+H]⁺ (ESI): 215.10. ¹H NMR (300 MHz, DMSO-d6) δ 10.76 (s, 1H), 7.49 (d, J=7.8 Hz, 1H), 7.32 (d, J=8.1 Hz, 1H), 7.13 (d, J=2.4 Hz, 1H), 7.07-7.02 (m, 1H), 6.98-6.93 (m, 1H), 2.87-2.82 (m, 2H), 2.69-2.64 (m, 2H), 2.59-2.50 (m, 4H), 1.75-1.64 (m, 4H).

12. Synthesis of 1-2-11

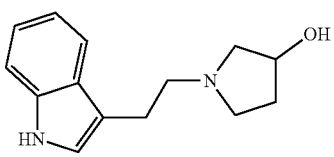

1-2-11

In a similar manner described for 1-2-1, compound 1-2-11 was prepared from 100 mg of 1-2 and 164.4 mg of 3-Pyrrolidinol. 5.5 mg (4%) of 1-2-11 (racemate) was obtained as a white solid. MS m/z [M+H]⁺ (ESI): 231.05. ¹H NMR (300 MHz, DMSO-d6) δ 10.75 (s, 1H), 7.49 (d, J=7.8 Hz, 1H), 7.32 (d, J=7.8 Hz, 1H), 7.13 (s, 1H), 7.07-7.02 (m, 1H), 6.98-6.93 (m, 1H), 4.67 (s, 1H), 4.19 (s, 1H), 2.84-2.73 (m, 3H), 2.67-2.58 (m, 3H), 2.45-2.34 (m, 2H), 2.01-1.95 (m, 11H), 1.56-1.51 (m, 1H).

13. Synthesis of 1-2-12

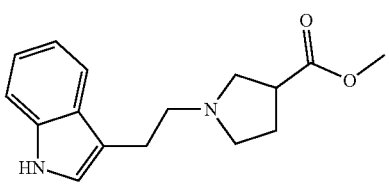

1-2-12

In a similar manner described for 1-2-6, compound 1-2-12 was prepared from 100 mg of 1-2 and 243.8 mg of methyl 3-pyrrolidinecarboxylate. 34.1 mg (20%) of 1-2-12 was obtained as a brown solid. MS m/z [M+H]⁺ (ESI): 273.05. ¹H NMR (300 MHz, DMSO-d6) δ 10.77 (s, 1H), 7.50 (d, J=7.8 Hz, 1H), 7.32 (d, J=8.1 Hz, 1H), 7.14 (d, J=2.1 Hz, 1H), 7.07-7.02 (m, 1H), 6.98-6.93 (m, 1H), 3.62 (s, 3H), 3.08-2.98 (m, 1H), 2.86-2.79 (m, 3H), 2.72-2.53 (m, 5H), 2.04-1.91 (m, 2H).

14 Synthesis of 1-2-13

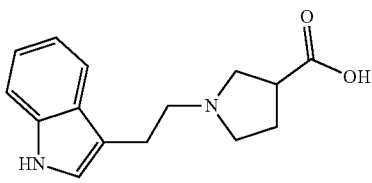

1-2-13

In a similar manner described for 1-2-1, compound 1-2-13 was prepared from 100 mg of 1-2 and 217.3 mg of methyl 3-Pyrrolidinecarboxylic acid. 24.0 mg (15%) of 1-2-13 was obtained as a white solid. MS m/z [M+H]⁺ (ESI): 259.05. ¹H NMR (300 MHz, DMSO-d6) δ 10.80 (s, 1H), 7.50 (d, J=6.9 Hz, 1H), 7.32 (d, J=7.5 Hz, 1H), 7.14 (s, 1H), 7.08-6.93 (m, 2H), 2.84-2.55 (m, 9H), 1.95 (s, 2H).

15. Synthesis of 1-2-14

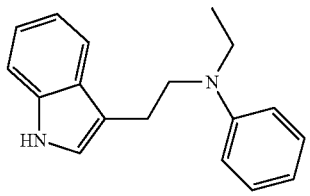

1-2-14

In a similar manner described for 1-2-1, compound 1-2-14 was prepared from 100 mg of 1-2 and 228.7 mg of N-Ethylaniline. 6.3 mg (4%) of 1-2-14 was obtained as a white solid. MS m/z [M+H]⁺ (ESI): 265.10. ¹H NMR (300 MHz, DMSO-d6) δ 10.84 (s, 1H), 7.55 (d, J=6.6 Hz, 1H), 7.35 (d, J=7.2 Hz, 1H), 7.22-7.15 (m, 3H), 7.11-6.96 (m, 2H), 6.72 (d, J=6.9 Hz, 2H), 6.60-6.54 (m, 1H), 3.55-3.49 (m, 2H), 3.41-3.35 (m, 2H), 2.95-2.90 (m, 2H), 1.11-1.06 (m, 3H).

16. Synthesis of 2-1-2

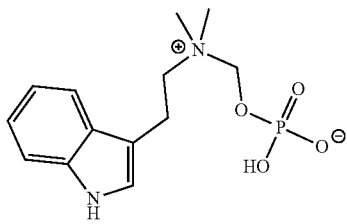

To a solution of tryptamine (200 mg, 1.25 mmol, 1.0 equiv) in 3 mL of methanol was added sodium cyanoborohydride (196.9 mg, 3.13 mmol, 2.50 equiv), acetic acid (0.15 mL) and formaldehyde (253.8 mg, 3.13 mol, 2.5 equiv, 37% in aq. soln) in methanol (1.5 mL) at 0° C. The mixture solution was stirred for overnight at 25° C. and then concentrated under vacuum. The resulting solution was diluted with 20 mL of saturated sodium bicarbonate and extracted with 3×20 mL of ethyl acetate. The combined organic layer was washed with 2×20 mL of brine, dried over anhydrous sodium sulfate and concentrated under vacuum. The resulting mixture was dissolved in 2 mL of acetonitrile, then di-tert-butyl (chloromethyl) phosphate (273.5 mg, 1.06 mmol, 2.0 equiv), Me₅-piperidine (164.5 mg, 1.06 mmol, 2.0 equiv) and sodium iodide (8.0 mg, 0.05 mmol, 0.1 equiv) was added at 25° C. under nitrogen atmosphere. The mixture was stirred for 24 h at 40° C. The resulting solution was diluted with 20 mL of ethyl acetate and washed with 2×10 mL of saturated sodium bicarbonate solution and 10 mL of saturated sodium chloride solution respectively. The combined organic layer was washed with 2×20 mL of brine, dried over anhydrous sodium sulfate and concentrated under vacuum. The crude product was used in the next step directly without further purification. 120 mg of 2-1-1 an intermediate phosphate was obtained as a white solid, which was used directly for the next reaction without further characterization.

To a solution of 2-1-1 (120 mg, 0.29 mmol, 1.0 equiv) in dichloromethane (1.2 mL) with an inert atmosphere of argon was added trifluoroacetic acid (0.6 mL) slowly at room temperature. The resulting solution was stirred for 1 h at room temperature. The resulting solution was concentrated under reduced pressure. The crude product was purified by Flash with the following conditions: Column, C18 silica gel; mobile layer, water and methanol (20% methanol up to 100% in 15 min and hold 100% for 5 min); Detector, 220 nm. The fractions were concentrated under reduced pressure. 28.3 mg (27.6% yield) of 2-1-2 was obtained as a white solid. MS m/z [M+H]⁺ (ESI): 299.05. ¹H NMR (300 MHz, DMSO-d₆) δ 11.11 (s, 1H), 7.65 (d, J=7.8 Hz, 1H), 7.37 (d, J=8.1 Hz, 1H), 7.26 (s, 1H), 7.11-6.98 (m, 2H), 4.89 (d, J=8.7 Hz, 2H), 3.51-3.45 (m, 2H), 3.18-3.13 (m, 2H), 3.07 (s, 6H). ³¹P NMR (121 MHz, DMSO-d₆) δ−1.88.

19. Synthesis of 3-1-4

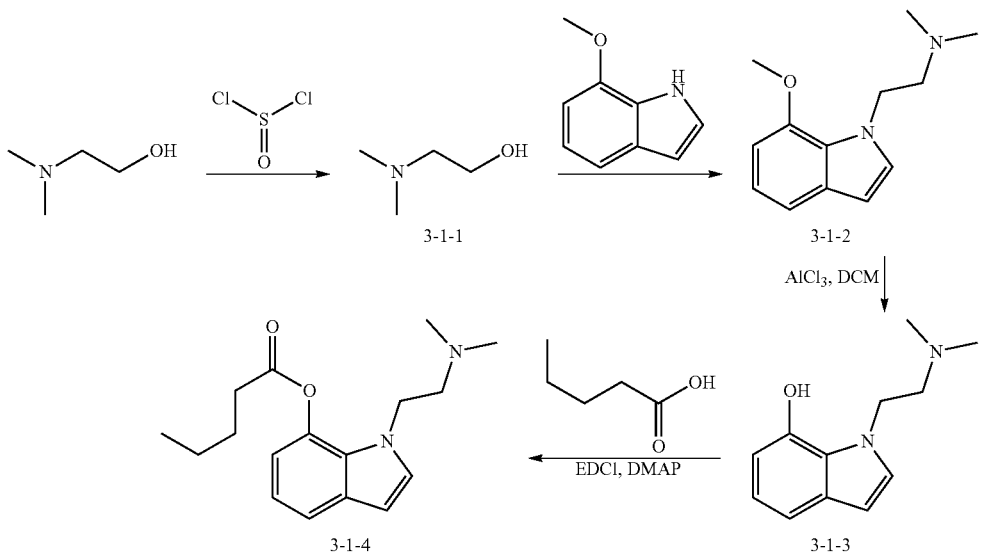

In a 250 mL flask in the ice bath, 12.83 g (0.11 mol, 1.1 equiv) of thionylchloride was added and then 8.91 g (0.10 mol, 1 equiv) of N,N-dimethyl ethanolamine was added dropwise over 0.5 h under stirring. The resulting mixture was stirred for 1 h at 50° C. Then 150 mL of ethanol was added and heated to reflux for 0.5 h, After cooling to room temperature, 3-1-1 (6 g, 42%) was collected by filtration as a light-yellow solid.

21. Synthesis of 3-1-2

A solution of 3-1-1 (6 g, 41.9 mmol, 1 equiv) in N,N-dimethylformamide (60 mL) was treated with KOH (11.75 g, 209.5 mmol, 5 equiv) for 1 h at 25° C. 7-methoxy-1H-indole (6.17 g, 41.9 mmol, 1 equiv) was added to the mixture at 25° C. The resulting mixture was stirred for 16 h at 50° C. The reaction was diluted with dichloromethane (200 mL), washed with water (3×200 mL). The organic phase was dried over anhydrous sodium sulfate, filtered and concentrated under reduced pressure. The crude product was purified by Flash with the following condition: Column, C18 silica gel; mobile layer, water (0.05% NH₄HCO₃) and acetonitrile (10% acetonitrile up to 100% in 20 min and hold 100% for 5 min); Detector, 220 nm. The fractions were concentrated under reduced pressure to afford 3-1-2 (5 g, 54%) as a white solid. MS m/z [M+H]$^+$ (ESI): 219.14.

22. Synthesis of 3-1-3

To a solution of 3-1-2 (600 mg, 2.75 mmol, 1 equiv) in dichloromethane (20 mL) was added aluminium chloride (1.83 g, 13.75 mmol, 5 equiv) in portions at 0° C. The mixture was stirred overnight at 25° C. The reaction was quenched with methanol (20 mL), filtered and concentrated under reduced pressure. The crude product was purified by Flash with the following condition: Column, C18 silica gel; mobile layer, water (0.1% NH$_3$·H$_2$O) and methanol (10% methanol up to 100% in 20 min and hold 100% for 5 min); Detector, 220 nm. The fractions were concentrated under reduced pressure. This resulted in 3-1-3 (415 mg, 73%) as a brown oil. MS m/z [M+H]$^+$ (ESI): 205.13.

23. Synthesis of 3-1-4

To a solution of 3-1-3 (100 mg. 0.49 mmol, 1 equiv) in dichloromethane (1 mL) was added pentanoic acid (75 mg, 0.74 mmol, 1.5 equiv), 4-dimethylaminopyridine (17.9 mg, 0.15 mmol, 0.3 equiv), N-(3-dimethylaminopropyl)-N'-ethylcarbodiimide hydrochloride (141.2 mg, 0.74 mmol, 1.5 equiv) at 25° C. The mixture was stirred for 2 h at 25° C. then diluted with 20 mL of dichloromethane, washed with 2×10 mL of saturated sodium bicarbonate solution and 2×10 mL of saturated aqueous sodium chloride respectively. The organic layer was dried over anhydrous sodium sulfate, filtered and concentrated under vacuum. The crude product was purified by Flash with the following condition: Column, C18 silica gel; mobile layer, water (0.05% NH$_4$HCO$_3$) and acetonitrile (20% acetonitrile up to 100% in 20 min and hold 100% for 5 min); Detector, 220 nm. The fractions were concentrated under reduced pressure. This resulted in 3-1-4 (22.6 mg, 16%) as a brown oil. MS m/z [M+H]$^+$ (ESI): 289.25. $^1$H NMR (300 MHz, Methanol-d4) δ 7.42-7.38 (m, 1H), 7.16 (s, 1H), 7.01-6.94 (m, 1H), 6.82-6.78 (m, 1H), 6.48-6.44 (m, 1H), 4.33-4.26 (m, 2H), 2.75-2.60 (m, 4H), 2.23 (s, 6H), 1.81-1.69 (m, 2H), 1.53-1.43 (m, 2H), 1.03-0.96 (m, 3H).

24. Synthesis of 4-1-2, 4-1-3, and 4-1-4

To a solution of tryptamine (400 mg, 2.5 mmol, 1.0 equiv) in 3 mL of methanol was added sodium cyanoborohydride (393.8 mg, 6.26 mmol, 2.50 equiv), acetic acid (0.3 mL) and formaldehyde (507.6 mg, 6.26 mol, 2.5 equiv, 37% in aq. soln) in methanol (4 mL) at 0° C. The mixture solution was stirred for overnight at 25° C. and then concentrated under vacuum. The resulting solution was diluted with 20 mL of saturated sodium bicarbonate and extracted with 3×20 mL of ethyl acetate. The combined organic layer was washed with 2×20 mL of brine, dried over anhydrous sodium sulfate and concentrated under vacuum. The resulting mixture dissolved in 3 mL of dichloromethane, then 483.5 mg of triethylamine was added, 1-chloroethyl carbonochloridate (340 mg, 2.39 mmol, 1.5 equiv) dropwise at 0° C. The mixture was stirred at 25° C. for 2 h. The reaction was diluted with dichloromethane (20 mL), washed with saturated aqueous sodium chloride (2×20 mL). The organic layer was dried over anhydrous sodium sulfate, filtered and concentrated under vacuum. 300 mg (crude) of 4-1-1 (intermediate) was obtained as a yellow solid. It was used for next step directly without further purification.

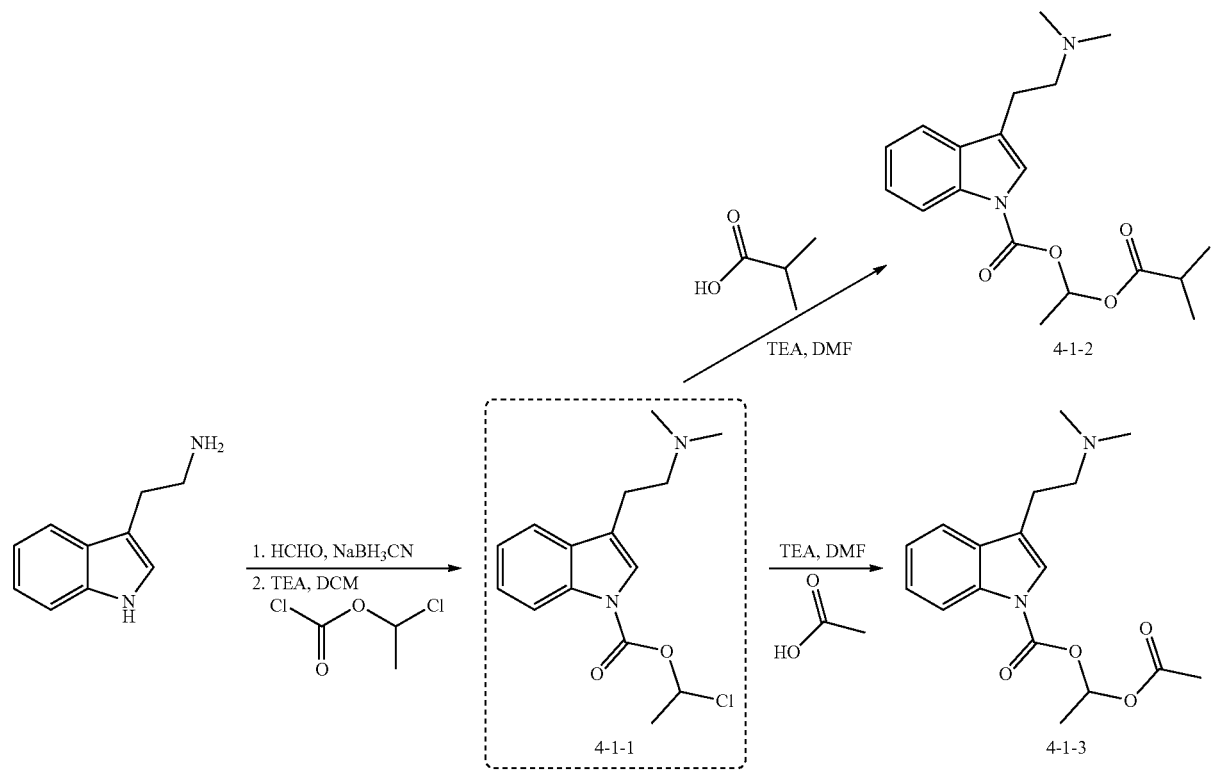

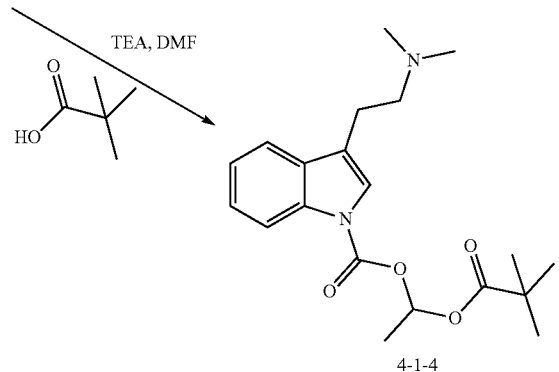

25. Synthesis of 4-1-2 (Racemate)

To a solution of 4-1-1 (300 mg, 1.02 mmol, 1.0 equiv) and triethylamine (2.06 g, 20.40 mmol, 20 equiv) in dimethylformamide (6 mL) was added isobutyric acid (449 mg, 5.10 mmol, 5 equiv) at 25° C. The mixture was stirred for 16 h at 60° C. The reaction was diluted with 50 mL of dichloromethane, washed with 1×50 mL saturated sodium chloride aqueous solution. The organic layer was dried over anhydrous sodium sulfate, filtered and concentrated under reduced pressure. The crude product was purified by Prep-HPLC for 2 times with the following condition: Column: X Select CSH Fluoro Phenyl, 30*150 mm, 5 μm; Mobile Phase A: Water (0.05% HCl), Mobile Phase B: ACN; Flow rate: 60 mL/min; Gradient: 28% B to 58% B in 8 min, 58% B; Wavelength: 254 nm; 9.0 mg of 4-1-2 was obtained as a light brown solid. Combined the other batches, 26 mg of 4-1-2 was obtained. MS m/z [M+H]$^+$ (ESI): 347.25. $^1$H NMR (300 MHz, DMSO-d6) δ 8.06 (d, J=8.1 Hz, 1H), 7.75-7.67 (m, 2H), 7.44-7.32 (m, 2H), 7.02-6.97 (m, 1H), 3.40-3.35 (m, 2H), 3.12-3.07 (m, 2H), 2.84 (s, 6H), 2.66-2.56 (m, 1H), 1.65 (d, J=5.4 Hz, 3H), 1.11 (d, J=7.2 Hz, 6H).

26. Synthesis of 4-1-3 (Racemate)

In a similar manner described for 4-1-2, compound 4-1-3 was prepared from 300 mg of 4-1-1 and 306 mg of acetic acid. 5.0 mg of 4-1-3 was obtained as a light brown solid. Combined the other batches, 40 mg of 4-1-3 was obtained. MS m/z [M+H]$^+$ (ESI): 319.10. $^1$H NMR (400 MHz, DMSO-d6) δ 10.16 (s, 1H), 8.08 (d, J=8.0 Hz, 1H), 7.75 (d, J=7.6 Hz, 1H), 7.65 (s, 1H), 7.43-7.32 (m, 2H), 7.01-6.97 (m, 1H), 3.39-3.33 (m, 2H), 3.15-3.11 (m, 2H), 2.83 (s, 6H), 2.10 (s, 3H), 1.63 (d, J=5.6 Hz, 3H).

27. Synthesis of 4-1-4 (Racemate)

In a similar manner described for 4-1-2, compound 4-1-4 was prepared from 300 mg of 4-1-1 and 520 mg of pivalic acid. The crude product (300 mg) was purified by Prep-HPLC with the following conditions (Column: XBridge Shield RP18 OBD Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 48% B to 78% B in 9 min, 78% B; Wavelength: 254 nm. 5 mg of 4-1-4 was obtained as oil. MS m/z [M+H]$^+$ (ESI): 361.25. $^1$H NMR (300 MHz, DMSO-d6) δ 8.03 (d, J=8.1 Hz, 1H), 7.65-7.62 (m, 1H), 7.51 (s, 1H), 7.39-7.26 (m, 2H), 6.98-6.93 (m, 1H), 2.83-2.78 (m, 2H), 2.57-2.54 (m, 2H), 2.20 (s, 6H), 1.64 (d, J=5.4 Hz, 3H), 1.17 (s, 9H).

28. Synthesis of 5-1-4

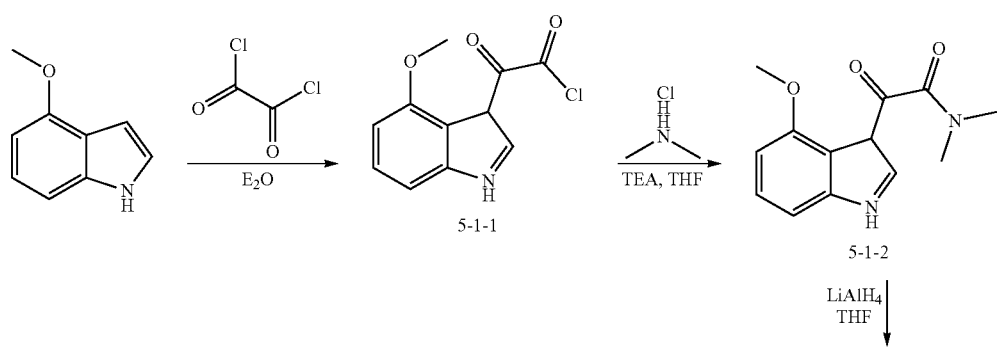

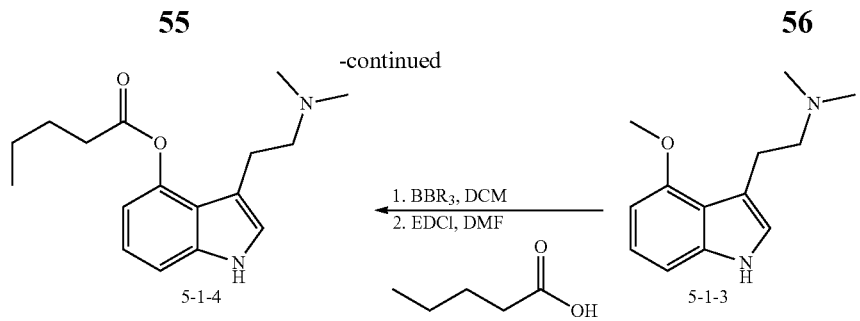

To a stirred solution of 4-methoxy-1H-indole (1.0 g, 6.80 mmol, 1.0 equiv) in diethyl ether (20.0 mL) was added oxalyl chloride (0.9 g, 6.80 mmol, 1.0 equiv) dropwise at 0° C. under nitrogen atmosphere. The resulting mixture was stirred for additional 3 h at room temperature. The resulting mixture 5-1-1 was used in the next step directly without further purification.

To a stirred solution of dimethylamine hydrochloride (1.7 g, 21.04 mmol, 5.0 equiv) and triethylamine (3.4 g, 33.66 mmol, 8.0 equiv) in tetrahydrofuran (10.0 mL) was added 5-1-1 (crude, obtained at last step) dropwise at 0° C. under nitrogen atmosphere. The mixture was stirred for additional 0.5 h at room temperature. The reaction was quenched by the addition of water (50 mL) at 0° C. The resulting mixture was extracted with ethyl acetate (3×50 mL). The organic layer was dried over anhydrous sodium sulfate, filtered and concentrated under vacuum. The crude was purified by Flash with the following condition: Column, C18 silica gel; mobile layer, water (0.05% NH$_4$HCO$_3$) and acetonitrile (10% acetonitrile up to 100% in 15 min and hold 100% for 5 min); Detector, 254 nm. 600 mg (58% yield) of 5-1-2 was obtained as a yellow solid. MS m/z [M+H]$^+$ (ESI): 247.10.

To a stirred solution of 5-1-2 (600.0 mg, 2.44 mmol, 1.0 equiv) in tetrahydrofuran (10.0 mL) was added Lithium Aluminum Hydride (184.9 mg, 4.87 mmol, 2.0 equiv) in portions at 0° C. The resulting mixture was stirred for 1.5 days at 70° C. The reaction was quenched by the addition of water (20.0 mL) at 0° C. The aqueous layer was extracted with ethyl acetate (3×30 mL). The organic layer was dried over anhydrous sodium sulfate, filtered and concentrated under vacuum. The crude was purified by Flash with the following condition: Column, C18 silica gel; mobile layer, water (0.1% NH$_3$·H$_2$O+10 mmol/L NH$_4$HCO$_3$) and acetonitrile (10% acetonitrile up to 100% in 15 min and hold 100% for 5 min); Detector, 254 nm. 350 mg (66% yield) of 5-1-3 was obtained as a yellow solid. MS m/z [M+H]$^+$ (ESI): 219.15.

To a stirred solution of 5-1-3 (80.0 mg, 0.37 mmol, 1.0 equiv) in dichloromethane (1.0 mL) was added tribromoborane (459.0 mg, 1.83 mmol, 5.0 equiv) dropwise at −78° C. under nitrogen atmosphere. The resulting mixture was stirred for 9 h at room temperature. The mixture was concentrated under vacuum. The residue was dissolved in dichloromethane (30.0 mL), added 50 mg of KHCO$_3$ and 15.0 mL of methanol. After stirring for 30 min, the resulting mixture was concentrated under reduced pressure. The resulting mixture was dissolved in N,N-dimethylformamide (1.0 mL), added entanoic acid (30.0 mg, 0.15 mmol, 1.0 equiv), N-(3-dimethylaminopropyl)-N'-ethylcarbodiimide hydrochloride (56.3 mg, 0.29 mmol, 2.0 equiv) and 4-dimethylaminopyridine (9.0 mg, 0.07 mmol, 0.5 equiv) at room temperature under nitrogen atmosphere. The resulting mixture was stirred for 16 h at room temperature. The reaction was diluted with ethyl acetate (3×10 mL), washed with water (3×10 mL). The organic phase was dried over anhydrous sodium sulfate, filtered, and concentrated under reduced pressure. The crude product was purified by Flash with the following condition: Column, C18 silica gel; mobile layer, water (0.05% NH$_4$HCO$_3$) and acetonitrile (10% acetonitrile up to 100% in 20 min and hold 100% for 5 min); Detector, 254 nm. This resulted in 5-1-5 (20.0 mg, 47%) as a colorless oil. MS m/z [M+H]$^+$ (ESI): 289.25. $^1$H NMR (300 MHz, DMSO-d$_6$) δ 11.03 (s, 1H), 7.23 (d, J=8.1 Hz, 1H), 7.15 (d, J=2.4 Hz, 1H), 7.06-7.01 (m, 1H), 6.66-6.63 (m, 1H), 2.78-2.65 (m, 4H), 2.47-2.43 (m, 2H), 2.20 (s, 6H), 1.73-1.63 (m, 2H), 1.48-1.35 (m, 2H), 0.94 (t, J=7.3 Hz, 3H).

Improved Prodrugs of Tryptamines, Such as N,N-dimethyltryptamine (DMT).

Prodrug 3-1-4, 4-1-2 and 4-1-4 was supposed to be stable in formulation and should release the parent compound in vivo.

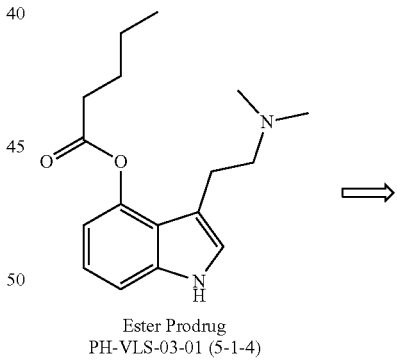

Ester Prodrug
PH-VLS-03-01 (5-1-4)

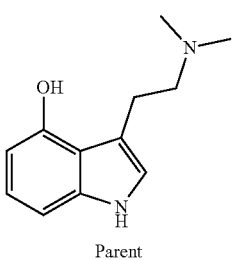

Parent

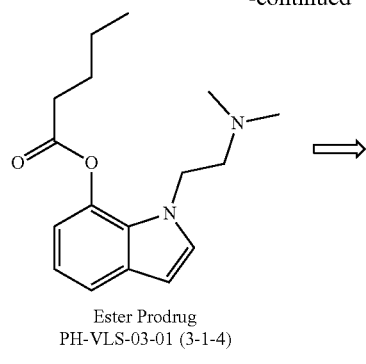

Ester Prodrug
PH-VLS-03-01 (3-1-4)

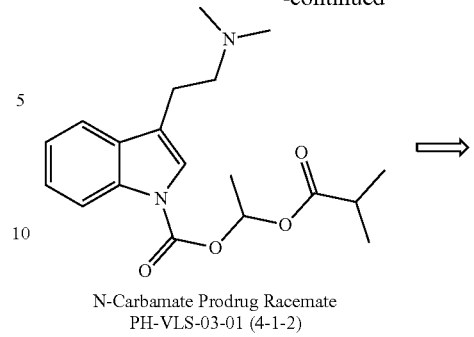

N-Carbamate Prodrug Racemate
PH-VLS-03-01 (4-1-2)

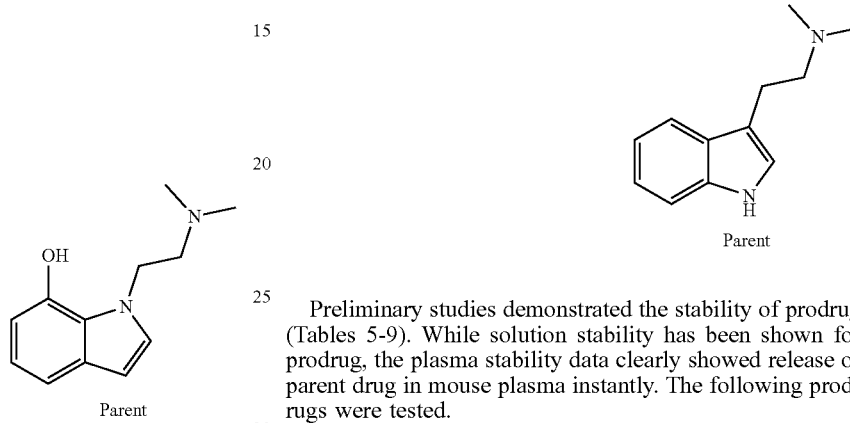

Parent

Parent

Preliminary studies demonstrated the stability of prodrug (Tables 5-9). While solution stability has been shown for prodrug, the plasma stability data clearly showed release of parent drug in mouse plasma instantly. The following prodrugs were tested.

Prodrugs 3-1-4, 4-1-2 and 4-1-4 Stability Results in PBS pH 6.5 with and without Pepsin

TABLE 5

Detection of VLS-03-1 Parent in PBS pH 6.5, SGF with and without pepsin

| | | | Peak Area of MRM: 205.0/159.8 | | | | | |
|---|---|---|---|---|---|---|---|---|
| Compound | Analyte | Incubation | VLS-03-1 standard | 0 min | 30 min | 60 min | 120 min | 240 min |
| VLS-03-1 | VLS-03-1 Parent | PBS (pH 6.5) | 4.49E+04 | 5.04E+04 | 4.71E+04 | 4.71E+04 | 4.86E+04 | 4.75E+04 |
| VLS-03-1 | VLS-03-1 Parent | SGF with pepsin | 4.22E+04 | 5.72E+04 | 5.37E+04 | 5.01E+04 | 5.48E+04 | 5.27E+04 |
| VLS-03-1 | VLS-03-1 Parent | SGF without pepsin | 3.75E+04 | 4.53E+04 | 4.75E+04 | 4.51E+04 | 4.66E+04 | 4.57E+04 |

TABLE 6

Detection of VLS-03-10 Parent in PBS pH 6.5, SGF with and without pepsin

| | | | Peak Area of MRM: 188.7/144.0 | | | | | |
|---|---|---|---|---|---|---|---|---|
| Compound | Analyte | Incubation | VLS-03-10 standard | 0 min | 30 min | 60 min | 120 min | 240 min |
| VLS-03-10 | VLS-03-10 Parent | PBS (pH 6.5) | 4.34E+03 | 5.32E+03 | 4.68E+03 | 5.00E+03 | 4.72E+03 | 4.95E+03 |
| VLS-03-10 | VLS-03-10 Parent | SGF with pepsin | 4.05E+03 | 5.13E+03 | 5.10E+03 | 5.25E+03 | 5.32E+03 | 5.28E+03 |
| VLS-03-10 | VLS-03-10 Parent | SGF without pepsin | 3.46E+03 | 5.29E+03 | 4.98E+03 | 4.66E+03 | 4.93E+03 | 4.61E+03 |

TABLE 7

Detection of VLS-03-15 Parent in PBS pH 6.5, SGF with and without pepsin

| | | | Peak Area of MRM: 205.0/159.8 | | | | | |
|---|---|---|---|---|---|---|---|---|
| Compound | Analyte | Incubation | VLS-03-15 standard | 0 min | 30 min | 60 min | 120 min | 240 min |
| VLS-03-15 | VLS-03-15 Parent | PBS (pH 6.5) | 6.74E+05 | 6.56E+05 | 6.55E+05 | 6.28E+05 | 5.86E+05 | 5.51E+05 |
| VLS-03-15 | VLS-03-15 Parent | SGF with pepsin | 6.26E+05 | 6.75E+05 | 7.21E+05 | 7.26E+05 | 7.14E+05 | 7.15E+05 |
| VLS-03-15 | VLS-03-15 Parent | SGF without pepsin | 6.10E+05 | 7.05E+05 | 6.94E+05 | 6.55E+05 | 7.09E+05 | 6.96E+05 |

Data Summary

TABLE 8

Stability results of test compounds in PBS pH 6.5, SGF with and without pepsin

| | | T½ | Remaining Percentage (%) | | | | |
|---|---|---|---|---|---|---|---|
| Compound | Incubation | (min) | 0 min | 30 min | 60 min | 120 min | 240 min |
| Chlorambucil | PBS (pH 6.5) | 47.25 | 100.00 | 64.51 | 42.26 | 16.83 | 2.99 |
| Erythromycin | SGF with pepsin | 43.62 | 100.00 | 56.55 | 37.33 | 14.06 | 2.14 |
| Erythromycin | SGF without pepsin | 39.47 | 100.00 | 52.67 | 28.46 | 8.27 | 1.47 |
| VLS-03-1 | PBS (pH 6.5) | 9999.00 | 100.00 | 96.32 | 99.71 | 100.03 | 101.35 |
| VLS-03-1 | SGF with pepsin | 8950.90 | 100.00 | 101.74 | 90.49 | 102.16 | 96.47 |
| VLS-03-1 | SIG F without pepsin | 9999.00 | 100.00 | 106.25 | 99.72 | 104.22 | 103.22 |
| VLS-03-10 | PBS (pH 6.5) | 19876.96 | 100.00 | 92.62 | 100.03 | 92.63 | 97.66 |
| VLS-03-10 | SGF with pepsin | 1604.11 | 100.00 | 96.82 | 93.09 | 91.42 | 89.32 |
| VLS-03-10 | SGF without pepsin | 7008.36 | 100.00 | 99.86 | 104.95 | 98.41 | 98.86 |
| VLS-03-15 | PBS (pH 6.5) | 922.46 | 100.00 | 96.93 | 89.82 | 89.44 | 82.54 |
| VLS-03-15 | SGF with pepsin | 9999.00 | 100.00 | 97.29 | 107.53 | 103.18 | 102.22 |
| VLS-03-15 | SGF without pepsin | 7839.52 | 100.00 | 101.12 | 103.35 | 105.28 | 97.98 |

If calculated T½ < 0, then T½ was reported as 9999 min.

Prodrugs 3-1-4, 4-1-2 and 4-1-4 Stability Results in Mouse Plasma

TABLE 9

Stability Results of Test Compounds in Mouse Plasma

| | | T½ | Remaining Percentage (%) | | | | |
|---|---|---|---|---|---|---|---|
| Compound | Species | (min) | 0 min | 15 min | 30 min | 60 min | 120 min |
| Propantheline | Mouse | 32.60 | 100.00 | 85.78 | 70.74 | 29.46 | 8.74 |
| VLS-03-1 | | N.A. | 100.00 | 0.00 | 0.00 | 0.00 | 0.00 |
| VLS-03-10 | | N.A. | 100.00 | 0.00 | 0.00 | 0.00 | 0.00 |
| VLS-03-15 | | N.A. | 100.00 | 0.00 | 0.00 | 0.00 | 0.00 |

N-Phosphonooxymethyl Prodrug 6-1-2 (PH-VLS-02-23-0)

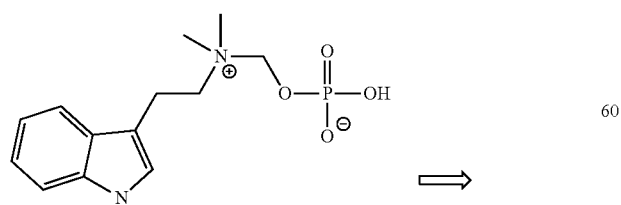

N-Phosphonoxymethyl Prodrugs
6-1-2

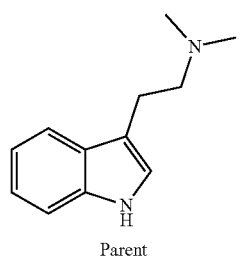

Parent

Using methods described in Gunda I. George (*Journal of Medicinal Chemistry*, 1999, Vol. 42, 3095) N-Phosphonooxymethyl Prodrug compounds were prepared.

Illustration of the Prodrug Strategy:

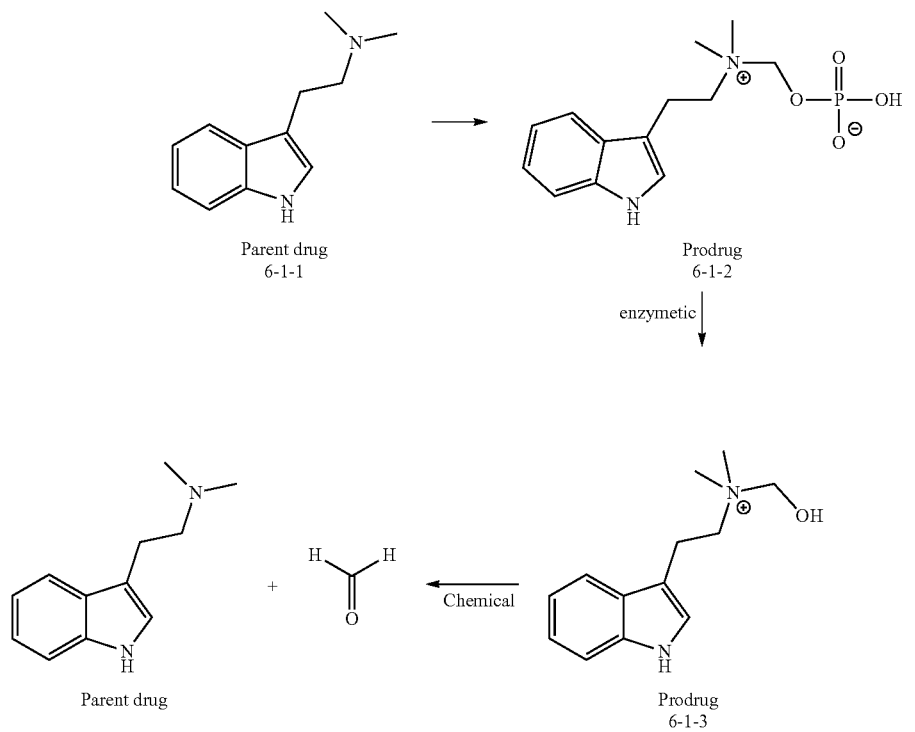

6-1-2 was synthesized, as a novel prodrug strategy for improving the water solubility of tertiary amine-containing drugs. And tertiary amine DMT was converted in two step reaction to a very polar, N-Phosphonooxymethyl Prodrug 6-1-3.

The prodrug 6-1-2 releases the parent DMT in vivo through a two-step bio-reversion process. The rate determining first step is via an enzymatic process, where prodrug bio-reversion involves a phosphatase-catalyzed dephosphorylation to give the resultant hydroxymethyl quaternary ammonium intermediate and inorganic phosphate. The second step involves conversion of hydroxymethyl quaternary ammonium intermediate chemically to DMT and formaldehyde at physiological pH.

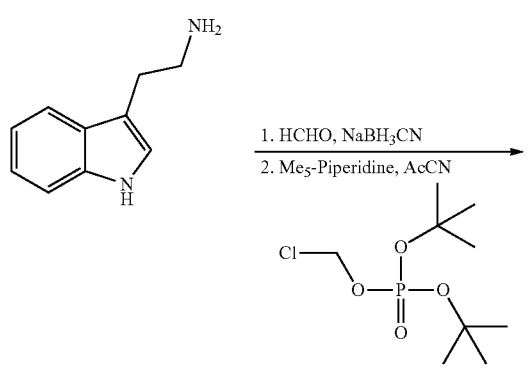

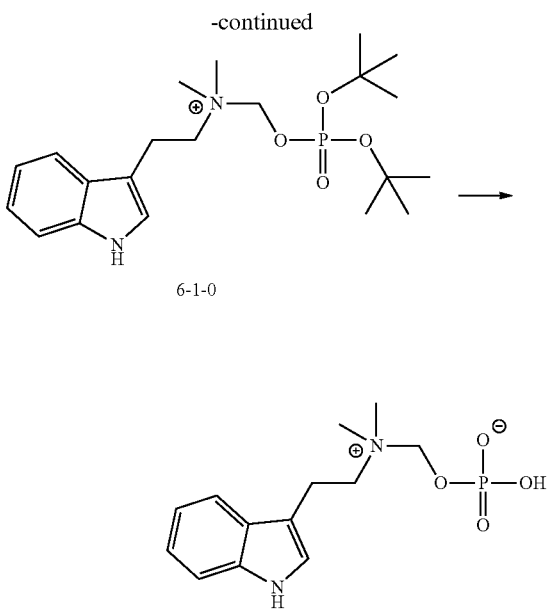

6-1-2 was synthesized, from commercially available in 3 simple steps.

Figure 2A:
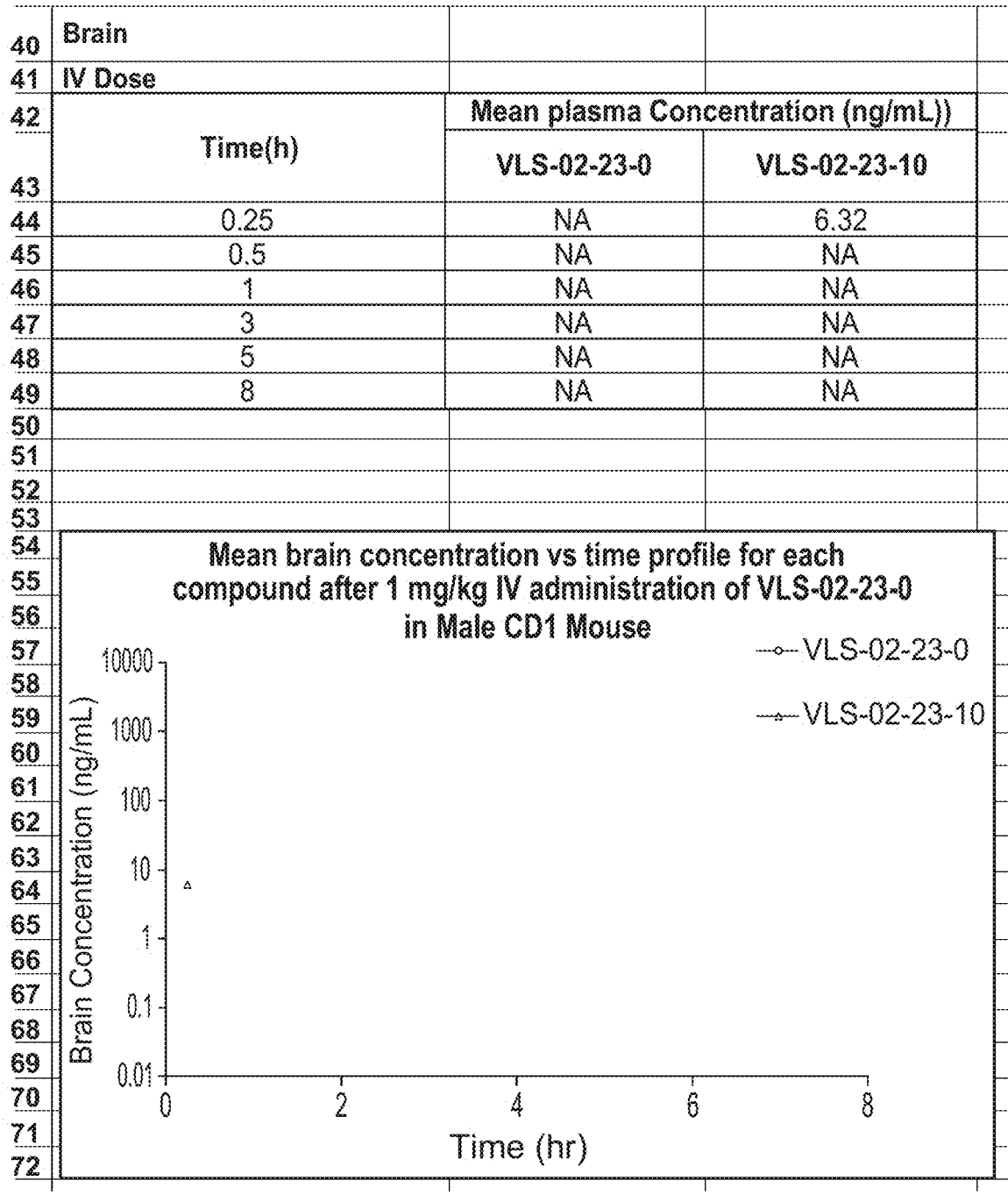
FIGS. 2A-2B show PK studies of N-phosphonooxymethyl prodrug 6-1-2 (VLS-02-23-0) and metabolite (OU LS-02-023-10) following intravenous (1 mg/kg) and oral administration (30 mg/kg) to male CD1 mice (in the brain).
Figure 2B:
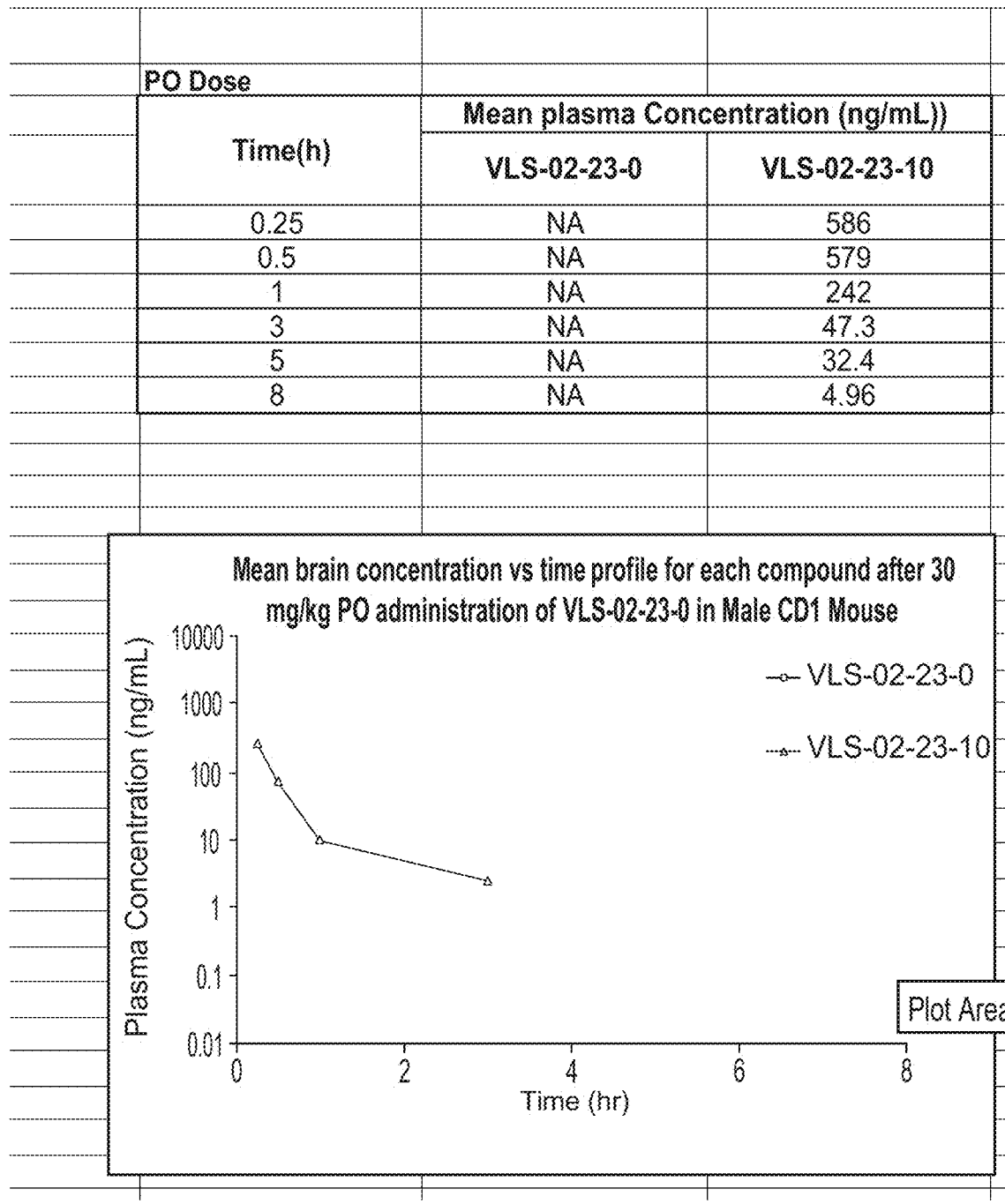

Chemical stability of prodrug 6-1-2 (VLS-02-23) was evaluated and the results enumerated in Tables 10-11. PK studies of prodrug 6-1-2 and metabolite (VLS-02-23-10) in mice were also conducted and both plasma exposure and brain exposure were analyzed as shown in FIGS. 1A-IC and FIGS. 2A-2B, respectively.

Chemical Stability of N-Phosphonooxymethyl Prodrug 6-1-2 (VLS-02-23) Data Summary

TABLE 10

Stability results of test compounds in PBS pH 6.5, SGF with and without pepsin

| Compound | Incubation | T½ (min) | Remaining Percentage (%) | | | | |
|---|---|---|---|---|---|---|---|
| | | | 0 min | 30 min | 60 min | 120 min | 240 min |
| Chlorambucil | PBS (pH 6.5) | 43.17 | 100.00 | 61.12 | 43.17 | 15.12 | 2.15 |
| Erythromycin | SGF with pepsin | 40.26 | 100.00 | 56.55 | 34.88 | 11.22 | 1.60 |
| Erythromycin | SGF without pepsin | 37.36 | 100.00 | 59.45 | 33.60 | 10.27 | 1.20 |
| VLS-02-23 | PBS (pH 6.5) | 9999.00 | 100.00 | 104.71 | 106.37 | 107.29 | 117.35 |
| VLS-02-23 | SGF with pepsin | 6227.35 | 100.00 | 96.70 | 106.43 | 102.36 | 96.82 |
| VLS-02-23 | SIG F without pepsin | 9999.00 | 100.00 | 98.76 | 107.08 | 101.90 | 108.80 |

Plasma Stability of N-Phosphonooxymethyl Prodrug 6-1-2 (VLS-02-23) Data Summary

TABLE 11

Stability Results of Test Compounds in Mouse Plasma

| Compound | Species | T½ (min) | Remaining Percentage (%) | | | | |
|---|---|---|---|---|---|---|---|
| | | | 0 min | 15 min | 30 min | 60 min | 120 min |
| Propantheline | Mouse | 34.09 | 100.00 | 80.81 | 64.04 | 34.86 | 9.05 |
| VLS-02-03 | | 568.34 | 100.00 | 114.24 | 110.21 | 109.95 | 91.16 |

What is claimed:

1. A compound of Formula:

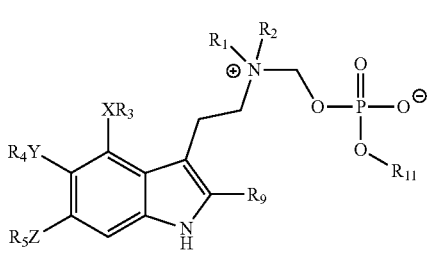

wherein $R_1$ and $R_2$ are independently hydrogen, alkyl, or cycloalkyl; or $R_1$ and $R_2$, together with the atoms to which they are attached form a heterocyclic ring;

X, Y, and Z are independently hydrogen, halogen, —O—, —S—, —NR$_4$—, or (P=O)—OR$_A$(—OR'), wherein R' and $R_A$ are independently hydrogen or alkyl;

$R_3$, $R_4$, and $R_5$ are independently absent, —(C=O)CHR$_7$(NH$_2$), —(C=O)CH(NH$_2$)(CH$_2$)$_n$(NH$_2$), or —(C=O)CH(NH$_2$)(CH$_2$)$_n$(NH)(C=NH)(NH$_2$);

$R_7$ is hydrogen or alkyl;

$R_9$ is hydrogen, alkyl, or halogen;

$R_{11}$ is a pharmaceutically acceptable cation, hydrogen, deuterium, alkyl, or cycloalkyl; and n is an integer from 2-7.

2. The compound of claim 1, wherein $R_1$ and $R_2$ are alkyl.

3. The compound of claim 1, wherein $R_1$ and $R_2$ are methyl.

4. The compound of claim 1, wherein $R_9$ is hydrogen.

5. The compound of claim 1, wherein $R_{11}$ is a pharmaceutically acceptable cation.

6. The compound of claim 1, wherein $R_{11}$ is hydrogen.

7. A compound of Formula:

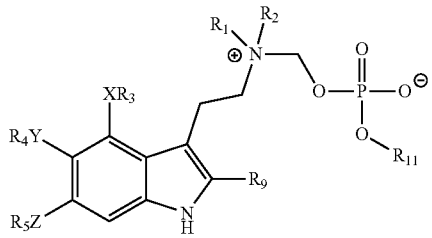

wherein $R_1$ and $R_2$ are independently hydrogen, alkyl, or cycloalkyl; or $R_1$ and $R_2$, together with the atoms to which they are attached form a heterocyclic ring;

X, Y, and Z are independently hydrogen, halogen, —O—, —S—, —NR$_4$—, or (P=O)—OR$_A$(—OR'), wherein R' and $R_A$ are independently hydrogen or alkyl;

$R_3$, $R_4$, and $R_5$ are independently absent, hydrogen, alkyl, —(C=O)-alkyl, —(C=O)(CH$_2$)$_n$(NH$_2$), —(C=O)(CH$_2$)$_n$(NH)(C=NH)(NH$_2$), or

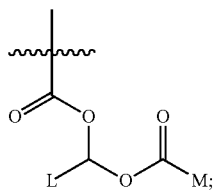

L and M are independently alkyl or aryl;

$R_9$ is hydrogen, alkyl, or halogen;

$R_{11}$ is a pharmaceutically acceptable cation, hydrogen, deuterium, alkyl, or cycloalkyl; and n is an integer from 2-7.

8. The compound of claim 7, wherein $R_1$ and $R_2$ are alkyl.

9. The compound of claim 7, wherein $R_1$ and $R_2$ are methyl.

10. The compound of claim 7, wherein $R_3$, $R_4$, and $R_5$ are absent.

11. The compound of claim 7, wherein $R_9$ is hydrogen.

12. The compound of claim 7, wherein $R_{11}$ is a pharmaceutically acceptable cation.

13. The compound of claim 7, wherein $R_{11}$ is hydrogen.

14. The compound of claim 7, wherein X, Y, and Z are hydrogen.

15. A compound of Formula (VIII):

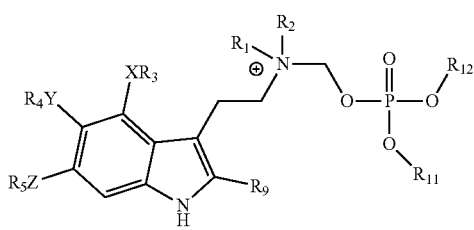

(VIII)

wherein:
$R_1$ and $R_2$ are independently hydrogen, alkyl, or cycloalkyl or $R_1$ and $R_2$, together with the atoms to which they are attached, form a heterocyclic ring;
X, Y, and Z are independently hydrogen, halogen, —O—, —S—, —$NR_A$—, or (P=O)—$OR_A$(—OR'), wherein R' and $R_A$ are independently hydrogen or alkyl;
$R_3$, $R_4$, and $R_5$ are independently absent, —(C=O)$CHR_7$(NH$_2$), —(C=O)CH(NH$_2$)(CH$_2$)$_n$(NH$_2$), or —(C=O)CH(NH$_2$)(CH$_2$)$_n$(NH)(C=NH)(NH$_2$);
$R_7$ is hydrogen or alkyl;
$R_9$ is hydrogen, alkyl, or halogen;
$R_{11}$ and $R_{12}$ are independently a pharmaceutically acceptable cation, hydrogen, deuterium, alkyl, cycloalkyl or $R_{11}$ and $R_{12}$, together with the atoms to which they are attached, form a heterocyclic ring; and
n is an integer from 2-7.

16. The compound of claim 15, wherein $R_1$ and $R_2$ are alkyl.

17. The compound of claim 15, wherein $R_1$ and $R_2$ are methyl.

18. The compound of claim 15, wherein $R_9$ is hydrogen.

19. The compound of claim 15, wherein $R_{11}$ is a pharmaceutically acceptable cation.

20. The compound of claim 15, wherein $R_{11}$ is hydrogen.

21. The compound of claim 15, wherein $R_{12}$ is a pharmaceutically acceptable cation.

22. The compound of claim 15, wherein $R_{12}$ is hydrogen.

23. A compound of Formula (VIII):

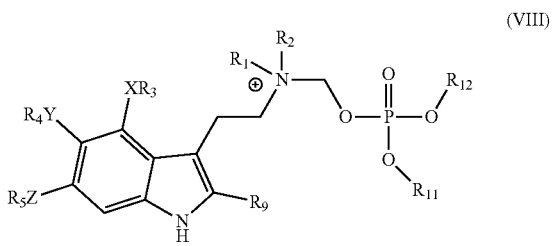

(VIII)

wherein $R_1$ and $R_2$ are independently hydrogen, alkyl, or cycloalkyl; or $R_1$ and $R_2$, together with the atoms to which they are attached form a heterocyclic ring;
X, Y, and Z are independently hydrogen, halogen, —O—, —S—, —$NR_A$—, or (P=O)—$OR_A$(—OR'), wherein R' and $R_A$ are independently hydrogen or alkyl;
$R_3$, $R_4$, and $R_5$ are independently absent, hydrogen, alkyl, —(C=O)-alkyl, —(C=O)(CH$_2$)$_n$(NH$_2$), —(C=O)(CH$_2$)$_n$(NH)(C=NH)(NH$_2$), or

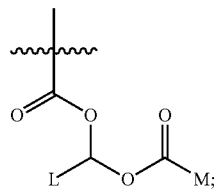

L and M are independently alkyl or aryl;
$R_9$ is hydrogen, alkyl, or halogen;
$R_{11}$ and $R_{12}$ are independently a pharmaceutically acceptable cation, hydrogen, deuterium, alkyl, cycloalkyl, or $R_{11}$ and $R_{12}$ together with the atoms to which they are attached form a heterocyclic ring; and
n is an integer from 2-7.

24. The compound of claim 23, wherein $R_1$ and $R_2$ are alkyl.

25. The compound of claim 23, wherein $R_1$ and $R_2$ are methyl.

26. The compound of claim 23, wherein $R_3$, $R_4$, and $R_5$ are absent.

27. The compound of claim 23, wherein $R_9$ is hydrogen.

28. The compound of claim 23, wherein $R_{11}$ is a pharmaceutically acceptable cation.

29. The compound of claim 23, wherein $R_{11}$ is hydrogen.

30. The compound of claim 23, wherein X, Y, and Z are hydrogen.

* * * * *